US006326154B1

(12) United States Patent
Carlsson et al.

(10) Patent No.: US 6,326,154 B1
(45) Date of Patent: *Dec. 4, 2001

(54) LIGAND-MEDIATED IMMUNOFUNCTIONAL HORMONE BINDING PROTEIN ASSAY METHOD

(75) Inventors: Lena Mariana Susann Carlsson, Gothenburg (SE); Ross Graham Clark, Pacifica; Wai Lee Tan Wong, Los Altos, both of CA (US)

(73) Assignee: Genentech, Inc., South San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/441,553

(22) Filed: May 15, 1995

Related U.S. Application Data

(63) Continuation of application No. 08/408,094, filed on Mar. 21, 1995, now abandoned, which is a continuation of application No. 08/039,093, filed as application No. PCT/US91/08664 on Nov. 19, 1991, now abandoned, which is a continuation-in-part of application No. 07/615,538, filed on Nov. 19, 1990, now Pat. No. 5,210,017.

(51) Int. Cl.[7] ........................ G01N 33/566; A61K 38/27; A61K 38/30
(52) U.S. Cl. ................................. 435/7.1; 514/2; 514/3; 514/4; 514/12
(58) Field of Search ................................. 514/2, 3, 4, 12; 435/7.1

(56) References Cited

U.S. PATENT DOCUMENTS

| 4,343,896 | 8/1982 | Wolters et al. . |
| 4,476,228 | 10/1984 | Huchzermeier et al. . |
| 4,486,530 | 12/1984 | David et al. . |
| 4,594,327 | 6/1986 | Zuk et al. . |
| 4,622,293 | 11/1986 | Ellis et al. . |
| 4,737,456 | 4/1988 | Weng et al. . |
| 4,837,381 | * 6/1989 | Steber et al. . |
| 4,849,227 | * 7/1989 | Cho . |
| 4,956,302 | 9/1990 | Gordon et al. . |
| 5,057,417 | * 10/1991 | Kanamondz et al. . |
| 5,096,885 | * 3/1992 | Pearlman et al. . |
| 5,126,324 | * 6/1992 | Clark et al. . |
| 5,130,298 | * 7/1992 | Cini et al. . |
| 5,210,017 | * 5/1993 | Carlsson et al. . |
| 5,593,844 | * 1/1997 | Carlsson et al. . |
| 5,688,763 | 11/1997 | Hammonds, Jr. et al. . |

FOREIGN PATENT DOCUMENTS

| 263 537 | 4/1989 | (DE) . |
| 369 943 | 5/1990 | (EP) . |
| WO 85/03357 | 8/1985 | (WO) . |
| WO 88/09818 | 12/1988 | (WO) . |
| WO 89/07271 | 8/1989 | (WO) . |
| 89/08667 | 9/1989 | (WO) . |
| 89/09792 | 10/1989 | (WO) . |
| 90/00569 | 1/1990 | (WO) . |

OTHER PUBLICATIONS

Amit et al., "A New and Convenient Assay of Growth Hormone–Binding Protein Activity in Human Serum" *Journal of Clinical Endocrinology and Metabolism* 71 (2):474–479 (1990).
Barnard et al., "Characterization of the growth hormone–binding protein of human serum using a panel of monoclonal antibodies" *J. Endocrinology* 123:327–332 (1989).
Baumann et al., "A rapid and simple assay for growth hormone–binding protein activity in human plasma" *Acta Endocrinologica* (Copenh) 119:529–534 (1988).
Baumann et al., "A Second, Lower Affinity Growth Hormone–Binding Protein in Human Plasma" *Journal of Clinical Endocrinology and Metabolism* 70(3):680–686 (1990).
Baumann et al., "A Specific Growth Hormone–Binding Protein in Human Plasma: Initial Characterization" *Journal of Clinical Endocrinology and Metabolism* 62(1):134–141 (1986).
Carlsson et al., "Ligand–Mediated Immunofunctional Assay for Quantitation of Growth Hormone–Binding Protein in Human Blood" *Journal of Clinical Endocrinology and Metabolism* 73(6):1216–1223 (1991).
Cunningham et al., "Receptor and Antibody Epitopes in Human Growth Hormone Identified by Homolog–Scanning Mutagenesis" *Science* 243:1330–1336 (1989).

(List continued on next page.)

*Primary Examiner*—Gary L. Kunz
*Assistant Examiner*—Stephen Gucker
(74) *Attorney, Agent, or Firm*—Knobbe, Martens, Olson & Bear, LLP

(57) ABSTRACT

A ligand=mediated immunofunctional assay (LIFA) method for detecting the presence and the concentration of polypeptide hormone binding proteins which comprises capturing the binding protein with a solid phase bound first antibody, saturating the bound hormone binding protein with the ligand polypeptide hormone, and detecting the bound ligand polypeptide hormone with a detectably labeled second antibody specific for the ligand polypeptide hormone. In the absence of added saturating polypeptide hormone, the LIFA measures the amount of hormone binding protein bound in the endogenous ligand polypeptide hormone. A growth hormone binding protein assay illustrates the method of the present invention. LIFA assay results indicate that increased binding protein substantially increases growth hormone activity. Methods of use and formulation of growth hormone binding protein, growth hormone, insulin-like growth factor-1 and insulin-like growth factor binding protein are disclosed.

9 Claims, 10 Drawing Sheets

OTHER PUBLICATIONS

Daughaday et al., "The Ontogeny of Serum GH Binding Protein in Man: A Possible Indicator of Hepatic GH Receptor Development" *Journal of Clinical Endocrinology and Metabolism* 65(5):1072–1074 (1987).

Emtner et al., "Identification and partial characterization of a growth hormone–binding protein in rat serum" *Acta Endocrinoligica* (Copenh) 122(3):296–302 (1990).

Herington et al., "Identification and Characterization of Specific Binding Proteins for Growth Hormone in Normal Human Sera" *J. Clin. Invest.* 77:1817–1823 (Jun. 1986).

Kipps et al., "Schemata for the production of monoclonal antibody–producing hybridomas" *Handbook of Exp. Immunology* (Chapter 108), Blackwell Science Pub. pp. 108.1–108.9 (1967).

Laron et al., "Serum GH Binding Protein Activities Identifies the Heterozygous carriers for Laron Type Dwarfism" *Acta Endocrinologica* 121:603–608 (1989).

Pekonen et al., "A Monoclonal Antibosy–Based Immunoradiometric Assay for Low Molecular Weight Insulin–Like Growth Factor Binding Protein/Placental Protein 12" *J. Immunoassay* 10(4):325–337 (1989).

Silbergeld et a., "Serum Growth Binding Protein Activity in Healthy Neonates, children and Young Adults: Correlation with Age, Height and Weight" *Clinical Endocrinology* 31:295–303 (1989).

Smith et al., "Gestational Profile and Affinity Cross–Linking of the Mouse Serum Growth Hormone–Binding Protein" *Endocrinology* 123(3):1489–1494 (1988).

Sumitomo et al., Database WPIL, Accession No. 88–363994, Derwent Publications pps. 5 (Nov. 10, 1988).

Ymer et al., "Binding Sites for Growth Hormone in Rabbit Placental Cytosol" *Endocrinology* 125(2):993–999 (1989).

Ymer et al., "Evidence for the specific binding of growth hormone to a receptor–like protein in rabbit serum" *Mol. and Cell. Endocrinology* 41:153–161 (1985).

Clemmons et al., *J. Cell Physiology* 145(1):129–135 (1990).

Yeoh, *Annals Acad. Med,* vol. 19, pp. 497–500, Jul. 1990.*

Baumann et al., *J. Clin. Endo. Metab.,* vol. 64, pp. 657–660, 1987.*

Baumann, G. *Trends Endocrinol. Metab.,* vol. 1/7 pp. 342–347, 1990, (Abstract Only).*

Baumann et al., *J. Clin. Endocrinol. Metab.,* vol. 65, pp. 814–816, 1987.*

* cited by examiner

- A  $y = -1.3584 + 1.0227x$  $R^2 = 0.994$
- B  $y = 0.21781 + 0.99084x$  $R^2 = 0.998$
- C  $y = 18.621 + 0.92695x$  $R^2 = 0.990$

LIGAND-MEDIATED IMMUNOFUNCTIONAL HORMONE BINDING PROTEIN ASSAY METHOD

This is a continuation of applications Ser. No. 08/408,094, filed on Mar. 21, 1995, now abandoned which is a continuation of Ser. No. 08/039,093, filed on Apr. 9, 1993, now abandoned, which is a 35 USC § 371 of PCT/US91/08664, filed on Nov. 19, 1991, which is a continuation-in-part of Ser. No. 07/615,538, filed on Nov. 19, 1990, now issued as U.S. Pat. No. 5,210,017, which applications are incorporated herein by reference and to which application priority is claimed under 35 USC § 120.

BACKGROUND OF THE INVENTION

1. Field of the Invention

A novel ligand-mediated immunofunctional assay (LIFA) method is described for detecting the presence and quantitating the amount of a polypeptide hormone binding protein in a biological fluid and/or determining the amount of the ligand polypeptide hormone specifically bound to the hormone binding protein. This modified immunometric assay for a hormone binding protein uses; 1) a first solid phase bound antibody to capture the hormone binding protein; 2) a saturating amount of ligand hormone; and, 3) a labeled second antibody specific for the ligand hormone. The LIFA method is exemplified by a growth hormone binding protein assay.

2. Description of the Background Art

A hormone binding protein (HBP) is a carrier protein found in biological fluids which has binding specificity for a ligand polypeptide hormone. Examples of such HBP's are growth hormone binding protein (GHBP), epidermal growth factor (EDG) binding protein, insulin-like growth factor 1 and 2 (IGF-1, IGF-2) binding proteins (six of them), platelet derived growth factor (PDGF) binding protein, nerve growth factor (NGF) binding protein, insulin binding protein, corticotropin releasing factor (CRF) binding protein, transforming growth factor beta (TGF-β) binding protein and activin binding protein (Follistatin).

One of the best characterized polypeptide hormone binding proteins is the GHBP. The GHBP discussed in this invention is the extracellular domain of the GH receptor which circulates in blood and functions as a GHBP in several species (Ymer, S. I, and Herrington, A. C., Mol. Cell. Endocrinol. 41:153 [1985]; Smith, W. C. and Talamantes, F., Endocrinology 123:1489–94 [1988]; Emtner, M., and Roos, P., Acta Endocrinologica [Copenhagen] 122:296–302 [1990]), including man (Baumann, G. et al., J. Clin. Endocrinol. Metab. 62:134–141 [1986]; Herington, A. C. et al., J. Clin. Invest. 77:1817–1823 [1986]). Little is known about the late of the GHBP or its regulation in various physiological and pathological conditions.

Hormone binding proteins have been assayed by antibody based precipitation methods where the ligand is labeled and the antibody is specific for the binding protein itself. Monoclonal antibodies specific for human growth hormone binding protein (hGHBP) were used by Barnard et al., J. Endocrinol, 123(2):327–32[1989]; for rabbit GHBP by Ymer et al., Endocrinology, 125(2):993–9[1989]; and mouse by Smith et al., Endocrinology 123(3):1489–94[1988]. Currently available methods for estimating GHBP levels in blood are based on incubation of the sample with radiolabeled GH, followed by separation of bound and free GH (Baumann, G. et al., Acta Endocrinologica (Copenhagen) 119: 529–34 [1988]; Amit, T. et al., J. Clin. Endo. Metab. 71:474–479 [1990]). The result obtained by these assays are difficult to interpret due to interference by endogenous GH (Baumann, G. et al., J. Clin. Endocrinol. Metab. 52:134–141 [1986]). Others who have used labeled growth hormone to detect GHBP are: Emther et al., Acta Endocrinol 122(3):296–302 (1990); Sibergeld et al., Clin. Endocrinol. 31(3):295–303 (1989); Daughaday et al., J. Clin. Endocrinol Metab. 65(5):1072–4, (1987); Herington et al., J. Clin. Invest. 77(6):1817–23. (19886); and Laron et al., Acta Endocrinol. 121(4):603–8 (1989). These assays for GHBP in blood have serious problems. They are laborious, requiring separation of complexed GHBP-GH by size-exclusion chromatography or antibody precipitation, and they may not give consistent results from one laboratory to another. In addition, they generate results that are arbitrary (i.e., not calibrated to a common protein standard) and influenced by endogenous growth hormone. Therefore, there is a need for an improved assay method which will allow detection of all the polypeptide hormone binding proteins, including those bound to endogenous polypeptide hormone.

Methods for the production of monoclonal antibody-producing hybridomas are disclosed by Kipps and Herzenberg in Clinical Endocrinology and Metabolism, Vol 62, No. 1, page 108.1–108.9 (1986)

A monoclonal antibody-based immunoradiometric assay for IGF binding protein was described by Pekonen et al., J. Immunoassay 10:325–37 (1989), immunometric or sandwich immunoassays using high affinity monoclonal antibodies were taught in David et al., U.S. Pat. No. 4,486,530. Such sandwich assays have an antigen with two or more epitopes sandwiched between two antibodies. Circulating proteins that bind non-polypeptide hormone ligands, such as the thyroxine binding protein, have been measured using fluorescent labeled tracer (U.S. Pat. No. 4,476,228) in order to determine the number of binding portion sites not occupied by thyroxine. Iodothyronine immunoassays in a biological fluid using blocking agents and thyroxine binding globulin were described in Gordon et al., U.S. Pat. No. 4,622,293.

Specific binding pairs (SBP) are discussed in reference to antigen-antibody reactions, ligand-receptor, hormone-receptor and lectin-oligosaccharide (U.S. Pat. No. 4,956, 302). Zuk et al., (U.S. Pat. No. 4,594,327) describes assays of whole blood to detect members of such SBPs wherein one member of the SBP must be attached to the solid phase prior to contacting the blood. The other second member of the SBP is detected using labeled second SBP member in competitive reactions. Similarly, Weng et al. (U.S. Pat. No. 4,737,456) describes a method of reducing interfering substances in assays of a SBP member wherein the individual member of the SBP is labeled. The receptor is used in a competitive assay to capture both labeled and unlabeled ligand, not to analyze for the presence of and quantity receptor as in the present invention. A method for the determination of an antigen using two antibodies is disclosed in U.S. Pat. No. 4,343,896.

Problems in Previous Polypeptide Hormone Binding Protein Assays

Problems in detecting HBP can be best illustrated by the problems encountered in detecting GHBP. Previous methods for determining the presence of GHBP in biological fluid were not as accurate as desired and frequently required the use of radioactive materials. The present invention avoids the problems of the previous assay methods in that it (a) does not require the use of radiolabeled GH; (b) does not require the removal of endogenous GH from the GHBP; (c) does not require any form of size separation of GH from the GH-GHBP complex; and, (d) measures the actual mass or absolute amount of GHBP rather than a relative amount reported in arbitrary units. The present invention has the added advantage that it measures the binding capacity of the circulating GHBP and is able to measure the degree of saturation of the GHBP with respect to GH. Moreover, the present invention is specific for GHBP by substantially reducing background assay noise that causes imprecision. The assay of the present invention avoids the problems in standard immuno-metric assays by using a first antibody to capture the GHBP and a second detectably labeled antibody to measure the presence of bound GH. The use of a second antibody specific the another epitope on the GHBP would not determine whether the GHBP was functional, and in addition, it could increase the background due to other serum proteins which bound both antibodies.

In order to study the function of the endocrine system it is essential to have access to reliable methods for quantitation of all parts of the system, i.e. the hormone, its binding protein and the hormone-binding protein complex. These measurements have not been previously achieved because of interference in the assays by the different components and the fact that both the hormone and the BP can be present in free and complexed forms. It is even more complicated when there are several different binding proteins for the same hormone, as for the IGF-1 system. However, the present invention teaches how the use of monoclonal antibodies directed at a specific binding protein can measure the amount and degree of saturation of that specific binding protein. In the case of GH, for which a second binding protein with lower affinity has been described (Baumann, G. and Shaw, M. A., J. Clin Endocrinol. Metab. 70:680–686 [1990]), this binding protein appears to be structurally unrelated to the GH receptor and should not be detected in our assay. However, this other GH binding protein may also be detected in the present invention's assay method once the other binding protein is isolated and appropriate antibodies are raised.

Currently, the standard method for quantitation of carrier proteins for peptide hormones is incubation of serum with the radiolabeled ligand, followed by chromatography or precipitation to separate the bound and free hormone. These procedures are laborious and the results often difficult to interpret because of the interference by endogenous hormone in the sample. These assay methods give an estimate of the binding capacity of serum proteins of a certain size but the activities of different binding proteins of similar size are not distinguished and the relative proportion of free and complexed BP cannot be determined. Another disadvantage is that the results are expressed in relation to reference serum pools, which makes it difficult to compare the results in different studies. In the present invention, we developed an assay for the GHBP by choosing a new approach. This assay was surprisingly able to precisely detect individual hormone binding proteins in a way that has not been previously demonstrated.

The LIFA, which is the preferred method used in the present invention, is simple to use and has the advantage that only functional binding protein is detected. When the assay method is applied to GHBP, both total and endogenously complexed GHBP are measured, and the assay does not require removal of endogenous GH from the GHBP or procedures to separate free GH from the GHBP complex. In contrast to previous methods, endogenous GH does not interfere in the assay; instead, bound GH, either endogenous or exogenously added, it used to detect the total and complexed GHBP, in fact, one cannot use the GH as the first member bound to the solid phase since GH cannot complex with binding protein that is already complexed with endogenous GH. Therefore, one requirement of the present assay method is for a solid phase coat antibody which recognizes the binding protein both in a free and complexed form. The assay method taught in this invention can also be used to measure the total binding capacity and the saturation of other polypeptide hormone-binding proteins with respect to the ligands that they bind.

Therefore, the present invention describes the development of a novel, sensitive and specific enzyme-linked immunosorbent assay (ELISA) for quantitation of biologically active HBP in biological fluids. The assay can also be used to measure the concentration of the ligand-hormone binding protein complex. The method of the present invention provides a number of advantages relating to ease of analysis, sensitivity, precision and reliability which will be more apparent as the details of the method are discussed.

SUMMARY OF THE INVENTION

A LIFA method is described for detecting the presence and the concentration of a polypeptide hormone binding protein and/or the degree of saturation of the hormone binding protein with its specific ligand hormone. Functional binding between the hormone binding protein and the ligand hormone is required in the assay. As illustrated in FIG. 1, steps 1–3, a monoclonal or polyclonal antibody which binds one or more hormone binding protein epitopes, which are exposed in both the free and the ligand hormone-associated binding protein, it used to capture the hormone binding protein on a solid matrix. In step 3, the captured hormone binding protein is incubated with the ligand hormone to saturate the hormone binding protein sites specific for the ligand hormone. In one option, the hormone binding protein is not saturated with the ligand hormone prior to the step 4 incubation with hormone specific labeled antibody. This allows determination of the level of endogenous ligand hormone associated with the hormone binding protein prior to incubation with added exogenous ligand hormone. The hormone binding protein and the ligand hormone may be simultaneously incubated together and with the solid phase capture antibody or they may be sequentially incubated with the capture antibody. In step 4, a detectably labeled monoclonal or polyclonal antibody, that binds to one or more epitopes on the ligand hormone at a site that is different from where the hormone binding protein binds, stably binds to the ligand hormone-hormone binding protein complex. When the hormone binding protein is saturated with added hormone (step 3) the total amount of detected hormone is a measure of the amount of binding protein present. When the hormone binding protein is not saturated with added hormone, the amount of detected hormone is a measure of endogenous ligand hormone associated with the hormone binding protein. A comparison of the two values allows a determination of both the amount of hormone binding protein present and the relative saturation with endogenous ligand hormone.

The therapeutic use of GHBP alone and in combination with GH to stimulate growth hormone responsive tissues is shown. The use of a GHBP-GH therapeutic composition is shown to result in greater stimulation of GH responsive tissues with the use of less GH. Furthermore, the GHBP-GH composition is longer lasting following administration thereby permitting less frequent administration than with GH alone.

DESCRIPTION OF THE PREFERRED EMBODIMENTS

Polypeptide Hormone Binding Protein Assay

Figure 1:
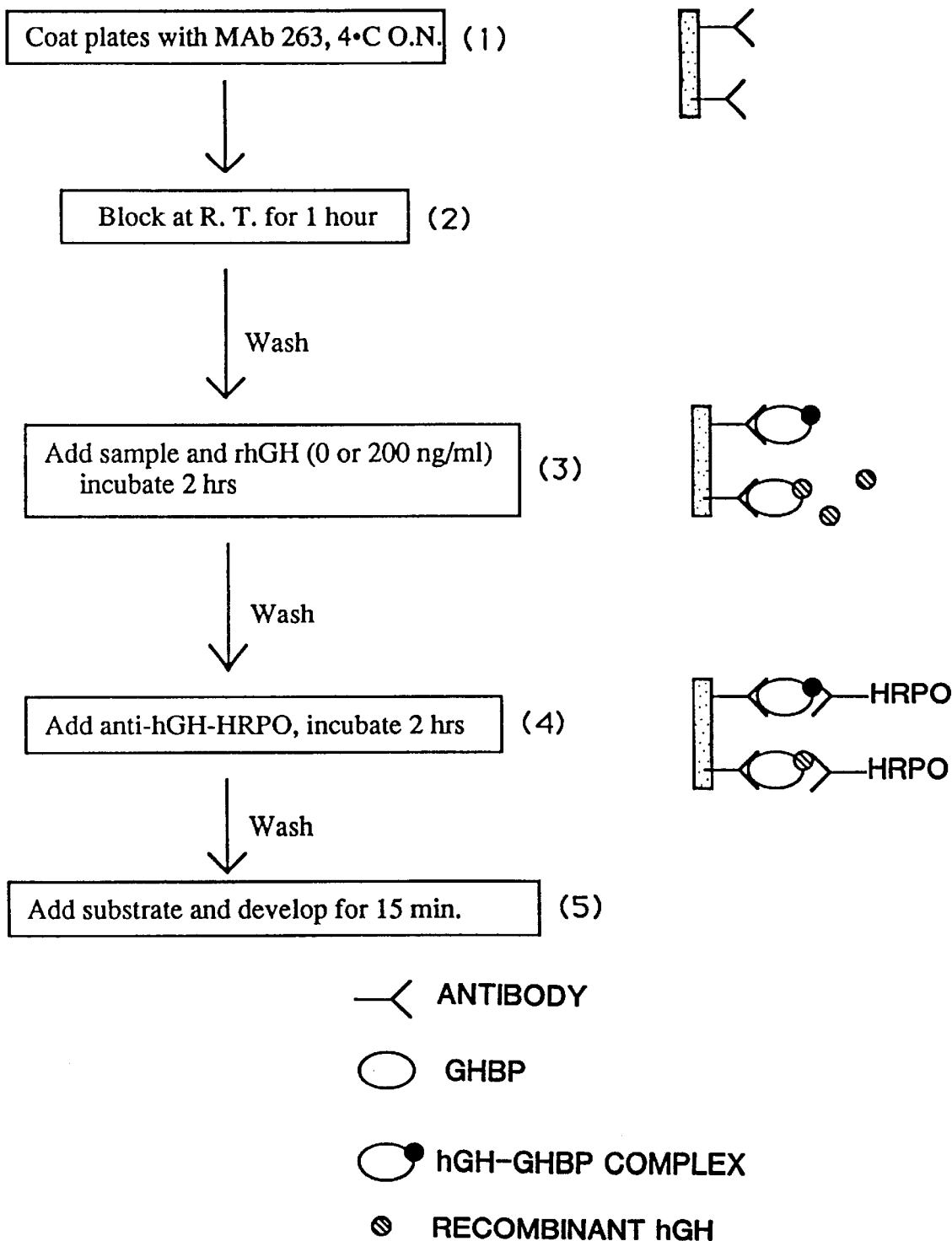
FIG. 1. Schematic of Assay Procedure for detecting human growth hormone binding protein.

Assaying for the presence of polypeptide hormone binding protein uses: (1) a first capture monoclonal antibody specific for the binding protein; (2) ligand polypeptide hormone and (3) a second monoclonal antibody specific for the ligand polypeptide hormone. The LIFA we have developed is a simple and sensitive method which allows quantitation of the total concentration of functional hormone binding protein in a solution. The assay's binding protein detection range may vary from about 4 to 20,000 pmol/L, more preferably from about 10 to 4000 pmol/L, and most preferably from about 20 to 2000 pmol/L. The assay can also be modified to measure the concentration of the circulating ligand hormone-binding protein complex. A monoclonal antibody directed against the binding protein, which recognizes both free and hormone bound binding protein is used to capture the binding protein on a solid phase, such as a microtiter plate. The samples are incubated with the ligand hormone to saturate all binding sites and an anti-hormone antibody is used to detect the amount of hormone (endogenous and exogenous) which has bound to the binding protein. The same procedure, but without incubation with ligand hormone, allows quantitation of the levels of circulating hormone-binding protein complex.

This LIFA may be used for any polypeptide hormone binding protein. It offers the ability to accurately detect the concentration of functional binding protein present in any biological fluid and to measure the endogeneous level of saturation of functional binding protein with its ligand polypeptide hormone. For the first time this assay method permits the measurement of functional HBP and the calibration of a HBP assay to a verifiable mass unit as opposed to serum units, etc. While this can be accomplished by using naturally produced HBP and ligand hormone (if available), it is usually accomplished by conducting the assay with recombinant polypeptide hormone and creating a standard curve based upon recombinant HBP. Surprisingly, the present LIFA method may be used to detect both the total HBP and the amount of HBP complexed with endogenous polypeptide hormone. Therefore, for the first time there is an accurate method of determining the amount of functional HBP which is not influenced by ambient polypeptide hormone.

In one modification of the present immunofunctional HBP assay method, the added ligand hormone contains a second delectable marker which does not hinder the binding of the detection antibody. This second marker on the ligand hormone and the first marker on the detection antibody are not the same. By separately measuring the amount of added ligand hormone bound and the amount of bound antibody, the percent saturation of the HBP with ligand hormone may be determined. The use of two distinct markers, one on the ligand hormone and one on the detection antibody, permits a simultaneous determination of the amount of bound exogenous ligand hormone and total HBP.

The assay of the present invention may also be used to quantitate the amount of ligand hormone in an unknown sample. Recombinant HBP, or HBP stripped of endogenous ligand hormone, is bound to the solid phase as in the assay method. First, the unknown sample containing the ligand hormone is contacted with the antibody bound HBP. Second, the ligand hormone specific labeled antibody is added and the amount bound is determined. This application of the LIFA permits the use of HBP in smaller amounts than would be used by directly coupling the HBP to the solid phase. The use of antibody to bind the HBP assures that the orientation is such that the HBP binding sites for the ligand hormone are not blocked.

Human Growth Hormone Binding Protein Assay

Assaying for the presence of hGHBP uses: 1) a first capture monoclonal antibody specific for the binding protein; 2) growth hormone; and 3) a second monoclonal antibody specific for growth hormone (FIG. 1). The LIFA we have developed is a simple and sensitive method which allows quantitation of the total concentration of functional growth hormone binding protein in biological fluids. The assay can also be modified to measure the concentration of the circulating ligand-binding protein complex. A monoclonal antibody directed against the growth hormone-binding protein, which recognizes both free and GH bound binding protein is used to capture the binding protein on a microliter plate (FIG. 1, step 1). The samples are incubated with human growth hormone to saturate all binding sites (FIG. 1, step 3) and an anti-hGH antibody is sued to detect the amount of hGH (FIG. 1, step 4) (endogenous and exogenous) which has bound to the binding protein. The same procedure, but without incubation with added hGH, allows quantitation of serum levels of circulating hGH-binding protein complex.

A preferred assay herein is a monoclonal antibody (MAb)-based sandwich ELISA for quantitation of GHBP in biological fluids such as human serum or plasma. The assay, which only detects functional GHBP, can be used to measure both total and complexed GHBP, and the degree of saturation of the GHBP with its ligand can therefore be calculated. In an assay developed for hGHBP, the 263 (coat) MAb binds free GHBP as well as GHBP bound to hGH, and is used to capture the GHBP on microtiter plates. The conjugates MAb MCB, which is directed against hGH, is used to detect the hGH that is bound to the immobilized GHBP. The total amount of GHBP is measured by saturating the binding sites with hGH, followed by detection of the total (endogenous and exogenous GH) bound to the GHBP. The concentration of the endogenous GH-GHBP complex is obtained by incubating the samples with the conjugated antibody without previous saturation of the GHBP and GH. The assay is sensitive and appears to cover the physiological range since random samples from 16 normal adults all had clearly detectable GHBP levels. Spike recovery experimetns show that the assay is useful for measuring GHBP level in both serum and plasma, with recoveries ranging from 89.1 to 113.6%.

One requirement of the present assay method is for a coat antibody which recognizes the antigen both in a free and complexed form, which the hGHBP is the MAb 263. Using the techniques described herein for generating such antibodies, we believe that the principle behind our GHBP LIFA could be used to measure the total binding capacity and the saturation of other polypeptide hormone-binding proteins. The difference in % bound observed when MAb 263 was tested in three different assay formats (FIG. 2) is due to the assay kinetics rather than the MAb binding characteristics. In the overnight pre-incubation experiment, the GHBP had the longest incubation with GH-$I^{125}$ and hence the highest % bound. Even though the reaction time (4 h) was the same in the simultaneous and the sequential assay, the complexing at GH-$I^{125}$ to GHBP would be faster for a homogeneous system (simultaneous) vs. a heterogeneous system (sequential), thus the % bound would be higher.

The GH used to saturate the GHBP may be a GH analog wherein there is a binding site specific for the GHBP and one or more exposed epitopes for binding the GH specific antibody.

Applications of the GHBP Assay

The results of the assay for GHBP and the degree of saturation of the GHBP with GH may be used for the diagnosis and treatment at growth deficiency. This assay is anticipated to provide an integrated index of the exposure of an organism to GH. It provides a more precise determination of total and free GH, which will better identity patients who are relatively GH-deficient and will benefit from GH replacement therapy. In general, the assay would be of value in any situation where GH is administered therapeutically for treating a clinical condition or where GH is present in excessive amounts and involved in causing or reflecting a clinical pathophysiology. The results provide an improved method for assessing compliance with GH replacement therapy and titrating does and individuallizing GH therapy for individual patients or those with particular clinical manifestations of GH deficiency or excess.

Use of these assay results facilitates diagnosing resistance to GH action due to decreased amounts of decreased binding activity of the GHBP or of the GH receptor, such as in hereditary or acquired syndromes. Hereditary syndromes, including Laron dwarfism and other syndromes of short status such as ideopathic short stature are revealed when abnormalities of the GHBP are shown to exist. The invention also assists in the identification and treatment of acquired syndromes including disease states where there is diminished or excessive expression of GHBP, such as in liver disease. Other examples of the use of the present assay invention include detection of diseases of ovarian function, diseases of joints or bone, or hypothalamic or plurality diseases causing excess GH or GHBP production. Clinical use of GHBP, or the GHBP/GH complexes as a therapeutic agent, are aided by the present invention because the measurement of GHBP or GHBP+GH after their administration assists clinical practice by allow a determination of the presence of therapeutically effective or therapeutically ineffective amounts in bodily fluids.

All parts of the growth promoting system are interrelated and it sis expected that administrating growth hormone releasing factor, growth hormone inhibitory factor (somatostatin), IGF-1, or IGF-1 binding proteins, may perturb GHBP concentrations. The measurement of GHBP assists clinical practice in assessing the suitability of patients for treatment with these proteins and the efficacy of such treatments.

Clinical Applications of GHBP Assay

Progress in our understanding of GHBP requires a quick, convenient and accurate assay for GHBP. The initial paper describing a GHBP was published in 1964 (Hadden et al., Nature 202:1342 [1964]). The serum GH-binding protein was better characterized in the mouse in 1977 (Peeters, S. and Friesen, H. G., Endocrinology 101:1164 [1977]), and in 1986 two groups further characterized the existence of a human serum-binding protein for GH (Baumann, G. et al., J. Clin. Endocrinol. Metab. 62:134–141 [1986]; Herington, A. C. et al., . Clin, Invest. 77:1817–1823 [1086]). When the GHBP was purified and characterized in the rabbit the amino-terminal 37 residues were shown to be identical to those of the extracellular part of the rabbit liver GH receptor (Spencer et al., J. Biol. Chem. 263:7862–7887 [1988]). It has been suggested that the GHBP derives from the membrane receptor by proteolytic cleavage (Trivedi and Daughaday, Endocrinology 123:2201 [1988]) or that it is produced from a separate mRNA derived from the same gene as the full-length GH receptor (Smith et al., Mol. Endo. p. 984 [1989]: Baumbach et al., Genes and Dev. 3:1199 [1989]). Studies of the ontogeny of the GHBP activity n man (Daughaday et al., J. Clin. Endocrinol, Metab. 66:1972–74 [1987]) and the changes in the concentrations of the GHBP and hepatic GH receptors in pregnant mice (Smith and Talamantes, Endocrinology 123:1489–94 [1988]) suggest that the serum GHBP levels could be a peripheral indicator of GH receptor activity.

This idea that GHBP levels reflect GH receptor activity is supported by the finding that patients with Laron-type dwarfism, a syndrome caused by the lack of functional GH receptors, also lack GH binding activity in serum (Daughaday and Trivedi, Proc. Natl. Acad. Sci. USA 84:4636–40 [1987]; Baumann et al., J. Clin. Endocrinol. Metabol 66:514–816 [1987]; Laron et al., Acta Endocrinologica (Copenhagen) 121:603–608 [1989]). There are indications that in some patients with Laron type dwarfism the abnormality is caused by partial deletion of the GH receptor gene (Godowski et al., Proc. Natl. Acad. Sci. USA 86:8083–8087 [1989]; Anselem et al., New England J. Med. 321–989–95 [1989]), which could result in growth failure due to inability to bind GH. For this type of abnormality our assay would be particularly useful since it, in contrast to some immunoassays, would not detect the inactive protein. The serum GH binding capacity is reduced in Laron-dwarfism heterozygotes, and it has been suggested that measurement of the hGHBP levels in serum could be of help for genetic counseling (Laron et al., supra).

Little is known about the physiological role of the GHBP, however, recent studies have shown that the binding protein can modify the effects of growth hormone. It has been demonstrated that the GHBP alters the distribution and half-life of GH (Baumann et al., Metabolism 38:330–333 [1989]), and there is also evidence to suggest that the GHBP affects the interaction of GH with the receptor of the target cells (Lim et al., Endocrinology 1276–1287 [1990]). It has recently been shown that recombination hGHBP produced in *E. coli* enhances the growth promoting effects of hGH when given to GH deficient rats, indicating that the GHBP may play an important role in the regulation of body growth in humans (see Example 5).

The LIFA of the present invention is used to monitor the concentration of GHBP in the biological fluids of a patient to detect aberrant concentration. In Example 5, 6 and 7 numerous applications of the assay are used to monitor and evaluate the activity of human GHBP alone and complexed with hGH. These pharmacological applications include purification, dosage, frequency of administration, and duration in circulation. The LIFA is also used to monitor the activity of hGHBP from different sources, such as *E. coli,* 293 cells or from natural tissue sources.

The LIFA has application in the pharmacologic evaluation of hGHBP action in primates. The hGHBP with, and without, complexed hGH can be monitored in primates to improve the dosage and frequency of administration.

In Primates

The ability of the GHBP to allow one to give infrequent GH injections, using similar GH does to those used currently, yet maintain growth responses, is of clinical significance. Experiments in the monkey, using the LIFA demonstrate that clearance of a GHBP+GH complex (in one of the forms described above or in a modified form), is delayed in primates. The clearance of injected GH bound to the GHBP is slowed to a degree similar to that which we have seen in the rat. This demonstrates in primates the improved growth promoting activities of administering hGH complexed to the hGHBP.

In primates, including humans, the GHBP-complex is able to be given at infrequent intervals, greater than every 2 days, more preferably at greater than every 7 days, without a loss of efficacy compared to injections of GH alone every 1 or 2 days or daily for a week or more. In addition, the GHBP complexed with GH or alone will be given at lower total weekly doses compared to GH alone. The undesirable side effects of GH treatment, for example the diabetogenic and fluid retaining properties of GH, will be reduced with the use of the GHBP. There are other beneficial effects of using GH-GHBP complex including a heightened IGF-1 response and the ability of the GHBP to direct GH preferentially to bone. This allows the GH-GHBP complex to be used for the treatment of bone disorders, including the prevention and treatment of osteroporosis. In each situation the LIFA is used to monitor the progress of the reaction. The dosages, formulations and methods of using and making hGHBP are described in U.S. Pat. No. 5,057,417.

The LIFA will be used to define groups of patients who have aberrant amounts of the GHBP complex. For example, a sub-set of poorly growing children, who are relatively resistant to the growth promoting activity of GH, will be found to be deficient in the GHBP. Such children include patients with Turner's Syndrome, kidney disease, as well as a class of binding protein deficient patients who were previously described as having iodiopathic short stature. Pharmacokinetic studies delivering the GHBP or GHBP-GH complex subcutaneously, and assay in the blood levels of GHBP-GH complex using the LIFA will be performed in man to establish suitable temporal dosing regimes. Doses of GH-GHBP complex sufficient to stimulate rises in IGF-1 concentrations in blood will be determined and these doses will indicate the doses of GHBP-GH complex necessary to induce body growth. Subsequently, long-term studies in the GH-resistant children will be initiated to demonstrate the ability of the GHBP-GH complex to stimulate whole body growth, including bone growth. The LIFA will be used to monitor blood levels of the GHBP.

A primary application of this invention is to use the GHBP LIFA to monitor endogenous levels of GHBP before and during treatment for GH or GHBP deficiency. The assay of this invention serves to direct the treatment that a patient undergoes. If there is no detectable GHBP in the blood, a Laron-type syndrome may be present and IGF-1 treatment indicated. If there is a low level of GHBP in the blood, additional GH or GHBP with or without IGF-1 may be indicated. Whatever treatment regime (GH or GH+IGF-1, or GH-GHBP complex treatment) instituted the LIFA will be most valuable to determine the GHBP response to treatment. Blood GHBP concentrations will rapidly reflect the efficacy of GH treatment much more so than measurement of traditional endpoints. A lack of response of blood GHBP levels will be used as a rapid diagnostic for considering alternative strategies for treatment.

Another use of the LIFA is to detect the biological activity of endogenous blood GH. This assay uses the addition of a constant amount of GHBP followed by the addition of sample without saturating with GH. It is anticipated that patients will be detected who possess high immuno-reactive but low immunofunctional concentrations of GH. A similar assay format can be used to measure the amount of bioactive GH in any sample, especially to test batches of recombinant GH for their biological activity.

The GHBP assay can be reversed to assay for GH. The captive antibody binds GH, GHBP is complexed and the indicator antibody is specific for the bound GHBP. This permits assay of GH alone or complexed with native GHBP.

Modes of Carrying Out the Invention

The present invention may be used to measure any known polypeptide hormone binding protein found in biological fluids. Similarly, it may be used with new hormone binding proteins as they are discovered. Among the preferred binding protein targets of the assay method of the present invention are the following: any growth, hormone binding protein, epidermal growth factor binding protein, insulin-like growth factor binding proteins, insulin binding protein, corticotropin releasing factor binding protein, nerve growth factor binding protein, transforming growth factor beta binding protein and activin binding protein. Detection of each of these binding proteins using the assay method of the present invention requires the use of their respective ligand polypeptide hormone to saturate the hormone binding sites on the binding protein. Polypeptide hormones may be purified from natural sources, produced by solid phase protein synthesis or produced by recombinant means. Among the preferred ligand polypeptide hormones used are: growth hormone, epidermal growth factor, insulin-like growth factor-1, insulin-like growth factor-2, nerve growth factor, insulin, corticotropin releasing hormone, transforming growth factor beta and activin. The preferred binding proteins and polypeptide hormones may be from any animal having such proteins in their biological fluids. The biological fluids may be any aqueous liquid such as the following: serum, plasma, lymph fluid, synovial fluid, follicular fluid, seminal fluid, amniotic fluid, milk, whole blood, urine, spinal fluid, saliva, sputum, fears, perspiration, mucus, tissue culture medium, tissue extracts and cellular extracts.

The pH of the medium will usually be in the range of about 4–11, more usually in the range of about 5–10, and preferably in the range of about 6.4–9.5. The pH is chosen so as to maintain a significant level of specific binding by the HBP and the polypeptide hormone, the binding of the antibodies and the requirements of the detectable label. In some instances, a compromise will be made among these three considerations. Various buffers may be used to achieve the desired pH and maintain the pH during the assay determination. Illustrative buffers include borate, phosphate, carbonate, Tris, barbital and the like. The particular buffer employed is not critical to this invention, but in individual assays one buffer may be preferred over another.

Moderate temperatures are normally employed for carrying out the assay method and usually constant temperatures are maintained during the period of the assay. The temperatures for the determination will generally range from about 4° to 50° C. more usually from about 15° to 40° C.

The concentration of HBP which may be assayed will generally vary from about $10^{-4}$–$10^{-15}$, more usually from about $10^{-6}$–$10^{-13}$M. While the concentrations of the various reagents will generally be determined by the concentration range of interest of the HBP, the final concentration of each of the reagents will normally be determined empirically to optimize the sensitivity of the assay over the range of interest.

The LIFA may be used to monitor clinical administration of hGHBP, either complexed with or without hGH. A preferred use of the assay method is in a method of promoting mammalian growth and anabolism comprising: (a) determining the optimal amount of a growth hormone binding protein required to promote a growth hormone induced response; (b) measuring by LIFA the amount of growth hormone binding protein present in the biological fluids of a person suspected of being deficient in said induced response; and, (c) comparing (a) with (b), and if (a) is greater than (b), administering growth hormone binding protein in an amount sufficient to increase the level of growth hormone binding protein to said optimal amount. Another preferred clinical application of the LIFA method is to monitor a growth hormone induced response such as weight gain, bone growth, muscle growth and function, organ growth and function, skin growth, and the level of IGF-1. The organs whose growth and function are stimulated may be thymus, kidney, liver, spleen, brain heart, lungs or gonads. Yet another application of the present LIFA method is for decreasing the frequency of injecting a growth promoting amount of a growth hormone binding protein-growth hormone complex comprising: (a) determining the minimum necessary serum level of growth hormone-growth hormone binding protein complex required to maintain optimal growth; (b) measuring by LIFA the level of growth hormone binding protein present in a patient suspected of being deficient in growth hormone binding protein-growth hormone complex; and, if the complex level in (b) is less than the level in (a), then, (c) administering an amount of growth hormone binding protein-growth hormone complex sufficient to maintain the level of complex for a period greater than two days. The period may be two to fourteen days, more preferably two to eight days, and most preferably three to seven days. The optimal amount of growth hormone binding protein is defined as that equal to or greater than 90% of the average level found in healthy individuals.

Antibodies

While polyclonal antibodies may be used, the preferred antibody is a monoclonal antibody. Monoclonal antibodies are highly specific, being directed against a single antigenic site. The antibody used in the present invention must be specific for epitopes which do not interfere or block the binding of the polypeptide hormone with the hormone binding protein. Therefore, the capture or coat antibody must bind to epitopes on the binding protein which leave the hormone binding site available for hormone binding. Similarly, the detection antibody must be specific for those polypeptide hormone epitopes which remain exposed following binding of the polypeptide hormone to the hormone binding protein. The antibodies may be made by methods commonly available to those of ordinary skill in the art. Methods for the production of polyclonal antibodies are described in numerous immunology tests, such as Microbiology, 3rd Edition, by Davis et al., Harper & Row, New York, 1980.

Monoclonal antibodies may be produced by the method first described by Kohler and Milstein, Eur. J. Immunol., 6:511 (1976). While the invention is demonstrated using mouse monoclonal antibodies, the invention is not so limited; monoclonals from any animal species will also function in the assay method of the present invention. In fact, in the present assay method, chimeric antibodies will also function. Chimeric antibodies are described in U.S. Pat. No. 4,816,567, Morrison et al., Proc. Natl. Acad. Sci. USA, 81:6851 (1984); Neuberger et al., Nature 312:604 (1984); Takeda et al., Nature 314:452(1985). Chimeric antibodies are made by splicing the genes from a mouse antibody molecule of appropriate antigen specificity together with genes from another animal encoding a second antibody. Similarly, monoclonal antibodies, or the antigen binding region of a monoclonal antibody, such as Fab or (Fab)$_2$ fragments, may be produced by recombinant methods. Both chimeric and recombinant antibodies or antibody fragments may be used in the assay method of the present invention.

The monoclonal antibodies can belong to any of the classes or subclasses of antibodies, including IgA, IgD, IgE, IgG, and IgM. Actively binding fragments of antibodies can also be employed, such as Fab, Fv, (Fab)$_2$, or the like. The monoclonal antibodies can be prepared by any convenient means which provides immortalization of the B-lymphocyte genes expressing the antibody sub-units, such as fusion between sensitized lymphocytes and a myeloid fusion partner; transformation, e.g., with Epstein-Barr virus (EBV); or other immortalization techniques. Alternatively, the genes can be isolated from a lymphocytic host expressing the antibodies and transferred to a more convenient host for expression in accordance with known genetic engineering techniques.

The antibodies may be obtained from any convenient vertebrate source, such as murine, primate, lagomorpha, bovine, ovine, equine, canine, feline or porcine. The antibodies are often prepared by fusing spleen cells from a host sensitized to the antigen with myeloma cell in accordance with known techniques or by transforming the spleen cells with an appropriate transforming vector to immortalize the cells. The cells can be cultured in a selective medium, cloned, and screened to select monoclonal antibodies that bind the designated antigens.

The methods used to produce the antibodies for the capture antibody and for the detection antibody may be conveniently made by administering the respective immunogen, either binding protein or polypeptide hormone, and eliciting antibody. The preferred antibody is monoclonal antibody. The antibody produced is then screened to determine the preferred antibody which does not hinder the binding reaction between the polypeptide hormone and the binding protein. The preferred monoclonal antibody for detecting the hGH when bound to hGHBP was produced by a mouse hybridoma (Cunningham et al., Science (1989) 243:1330–1336). The anti-hGHBP monoclonal antibody used as the capture or coat antibody is commercially available (Agen Inc., 90 East Halsey Road, Persippanyu N.J. 07054) or can be made using the hGHBP as immunogen and screening the antibody as discussed above.

Because of the relative ease with which antibodies can now be prepared against antigens, preferred embodiments of the present invention use monoclonal or polyclonal antibodies attached to the solid phase to capture the HBP. Techniques for attaching specific HBP to various solid phase substrates, such as filter, plastic etc. are well known and need not be described here in detail. See, for example, U.S. Pat. No. 4,376,110 and the references cited therein. Among the more preferred common solid phase supports are: small sheets, plastic beads, assay plates or test tubes made from polyethylene, polystyrene, polypropylene or other suitable material. Also useful are particular materials such as papers, agarose, cross-linked dextran, and other polysaccharides.

Interference by Heterophilic Antibodies

When results from GHBP assays using HRPO-conjugated MCB and HRPO-conjugated mouse polyclonal antibody were compared, one human serum sample showed much higher GHBP levels when detected with the MCB-conjugate. To test if the discrepancy could be due to heterophilic antibodies, purified mouse IgG (migG) at 0.5 mg/ml, was included in the sample buffer. The results showed that migG reduced the signal is sample #6 from 384 pmol/L to 215 pmol/L when assayed with the MAb-conjugate, while the GHBP concentrations were unchanged in two control samples (323 vs 338, 92 vs 111 pmol/L when assayed with and without migG respectively). These results indicate that the two different conjugated antibodies were substantially the same if the unspecific binding was blocked by the migG.

Sandwich type immunometric assays are subject to positive interference by heterophilic antibodies in the sample. This is caused by human anti-mouse antibodies in the human serum sample. Such heterophilic antibodies crosslink the coat and the conjugate mouse antibodies. Interference by heterophilic antibodies can be diminished or eliminated if immunoglobulins from a nonimmunized animal (here to HBP or ligand hormone) are added to the assay to block the heterophilic antibodies in the sample. In act, the discrepancy in the GHBP concentration was eliminated when mouse IgG was included in the assay buffer. This indicated that the unspecific signal which was detected when the conjugated MAb was used was due to the presence of anti-mouse IgG antibodies in the serum from this subject. Since one doesn't know which samples will show this type of interference it is best to always include mouse IgG in the first step of the assay.

Deposit of Mybridoma

The hydridoma cell line producing this anti-hGH antibody is HGH-B which was deposited with the American Type Culture Collection (ATCC) 12301 Parklawn Drive, Rockville, Md. USA. on Nov. 9, 1990, and has ATCC Registration number HB-10596. this deposit was made under the provisions of the Budapest Treaty on the International Recognition of the Deposit of Microorganisms for the purpose of Patent Procedure and the Regulations thereunder (Budapest Treaty). This assures maintenance of the viable cultures for 30 years from the date of the deposit. The cells will be made available by the ATCC under the terms of the Budapest Treaty, and subject to an agreement between Genentech, Inc. and the ATCC, which assures permanent and unrestricted availability of the progeny of the cultures to the public upon issuance of the pertinent U.S. patent or upon laying open to the public of any U.S. or foreign patent application, whichever comes first, and assures availability of the progency to one determined by the U.S. Commissioner of Patents and Trademarks to be entitled thereto according to 35 USC 122 and the Commissioner's rules pursuant thereto (including 37 CFR 1.12 with particular reference to 886 OG 638).

The assignee of the present application has agreed that it the cultures on deposit should die or be lost or destroyed when cultivated under suitable conditions, they will be promptly replaced on notification with a viable specimen of the same culture. Availability of the deposited strain is not to be constructed as a license to practice the invention in contravention of the rights granted under the authority of any government in accordance with the patent laws.

Detactable Markers

Detectable markers or labels on the antibodies that may be covalently attached include a suitable indicator such as an enzyme, radioactive isotope, fluorescer, or other measurable tag as described in U.S. Pat. No. 4,275,149, bridging columns 19 to 28 and U.S. Pat. No. 4,318,980, columns 10–14. Of particular interest are enzymes which involve the production of hydrogen peroxide and the use of the hydrogen peroxide to oxidize a dye precursor to a dye. Particularly combinations include saccharide oxidases, e.g., glucose and galaclose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Among the preferred enzymes are the following: horseradish peroxidase, glucoamylase, alkaline phosphatase, glucose oxidase, and beta-D-galactosidase.

Additional enzyme combinations may be found in the subject matter disclosed in the cited references. When a single enzyme is used as a label, other enzymes may find use such as hydrolases, transferases, and oxidoreductases, preferably hyudrolases such as alkaline phosphatase and beta-galactosidase. Alternatively luciferases may be used such as firefly luciferase and bacterial luciferase (U.S. Pat. No. 4,737,458).

Following the use of antibody specific for the ligand hormone, the amount of bound antibody is determined by measuring the activity of the attached indicator. In the case of enzymes, the amount of color developed and measured will be a direct measurement of the amount of hormone or hormone binding protein present. The conjugation of such tags, including the enzymes, to an antibody as described herein is a standard manipulative procedure for one skilled in immunoassay techniques. See for example. O'Sullivan et al., (1981) Methods for the Preparation of Enzyme-Antibody Conjugates for use in Enzyme Immunoassay, In Methods in Enzymology (ed. J. J. Langone & H. Van Vunakis), Academic press, New York, Vol. 73, pp 147–166.

Kits

As a matter of convenience, the assay method of the present invention can be provided as a kit, i.e., a packaged combination with other reagent for combination with a sample or samples in assaying for a polypeptide hormone binding protein and/or to determine relative saturation with ligand polypeptide hormone. The components of the kit will be provided in predetermined ratios. The kit will contain the specific carrier acid phase for the capture antibody, capture antibody separate or bound to the carrier solid phase, the ligand hormone (preferably recombinant), and the detection antibody containing a detectable label. Where the detectable label is an enzyme, the it will include substrates and cofactors required by the enzyme, a dye precursor, which provides the detectable chromophore of fluorophore. In addition, other additives may be included such as stabilizers, buffers and the like. The relative amounts of the various reagents may be varied widely to provide for concentrations in solution of the reagents which substantially optimize the sensitivity of the assay. Particularly, the reagents may be provided as dry powders, usually lyophilized, including excipients, which on dissolution will provide for a reagent solution having the appropriate concentration for combining with the sample to be tested.

Definitions and Abbreviations:

Capture (coat) antibody: Antibody specific for hormone binding protein epitope such that binding of antibody does not hinder the binding of the ligand polypeptide hormone to the hormone binding protein. Antibody is attached to a solid phase and it is used to selectively bind to the binding protein and facilitate removal of the binding protein from a solution.

Detection antibody; Antibody which is labeled with detectable marker specific for an epitope on the polypeptide hormone and which is the detectable marker.

HBP: hormone binding protein; the carrier protein found in biological fluids that has affinity for a ligand polypeptide hormone and acts as a carrier for the bound ligand polypeptide hormone.

hGH: human growth hormone, including multiple naturally occurring forms such as 22 kd, 20 kd, placental variant (GHV), and variants produced by recombinant method (Cunningham et al., Science (1989) 243:1330–1336).

GHBP: growth hormone binding protein.

hGHBP: human growth hormone binding protein;

GH: growth hormone,

MAb: monoclonal antibody,

MCB: Monoclonal B produced by the mouse hybridoma HGH-B;

HRPO: horse radish peroxidase.

BSA: Bovine serum albumin;

LIFA Ligand-mediated immunofunctional assay.

Purification of GHBP

The purification of the GHBP used is monitored using a conventional ELISA (Fuh, G. et al., J. Biol. Chem. 265, 3111–3115 [1990]). The LIFA of the present invention provides a better assay for detecting the presence and assaying the amount of functional binding protein during such a purification. The LIFA ensures that functional active binding protein rather than immunologically active binding protein is purified. During hGHBP storage the LIFA is used to follow the amount of functional GHBP that remains in an active form with time. This property of the assay greatly aids in satisfying regulatory requirements concerning the stability of the GHBP during prolonged storage.

Materials and Methods

Selection of coat MAb

Four monoclonal antibodies to the rabbit liver growth hormone receptor, MAbs 1, 2, 5 and 7 were provided by Dr. M. Waters (University of Queensland, Queensland, Australia), and an additional two MAbs (43 and 263) were purified from mouse ascites fluid purchased from Agen, Australia. Immulon II removawell (Dynatech Laboratories, Inc., Alexandria, Va.) were coated by incubating them overnight at 4° C. with antibody, 100 µL per well at 5 µg/mL in 50 mmol/liter carbonate buffer, pH 9.6 (coating buffer). After removing the coating solution, nonspecific binding sites on the coated plates were blocked with 150 µL of phosphate-buffered isotonic saline pH 7.2 (PBS) containing 5 g of bovine serum albumin (BSA) per liter (blocking buffer), for 1 h at room temperature, followed by three washes with wash buffer (0.5 mL of Tween 20 and 0:1 g of Thimerosal per liter of PBS). The immobilized MAbs were evaluated in three different experiments. In the first experiment, using sequential incubation steps, GHBP was first incubated with MAb coated on the well, followed by addition of radiolabelled GH (GH-I$^{125}$). In the second experiment the reaction of GHBP and GH-I$^{125}$ was carried out simultaneously in MAb coated wells. In the third experiment, GHBP was pre-incubated with hGH-I$^{125}$ overnight at 4° C. and then added to the MAb coated well. In all three experiments, the nonspecific binding of tracer was determined by substituting the GHBP solution in the reaction mixture with incubation buffer (PBS continuing per liter, 5 g of BSA, 0.5 mL of Tween 20 and 0.1 mL of Thimerosol).

Sequential Assay

Figure 6:
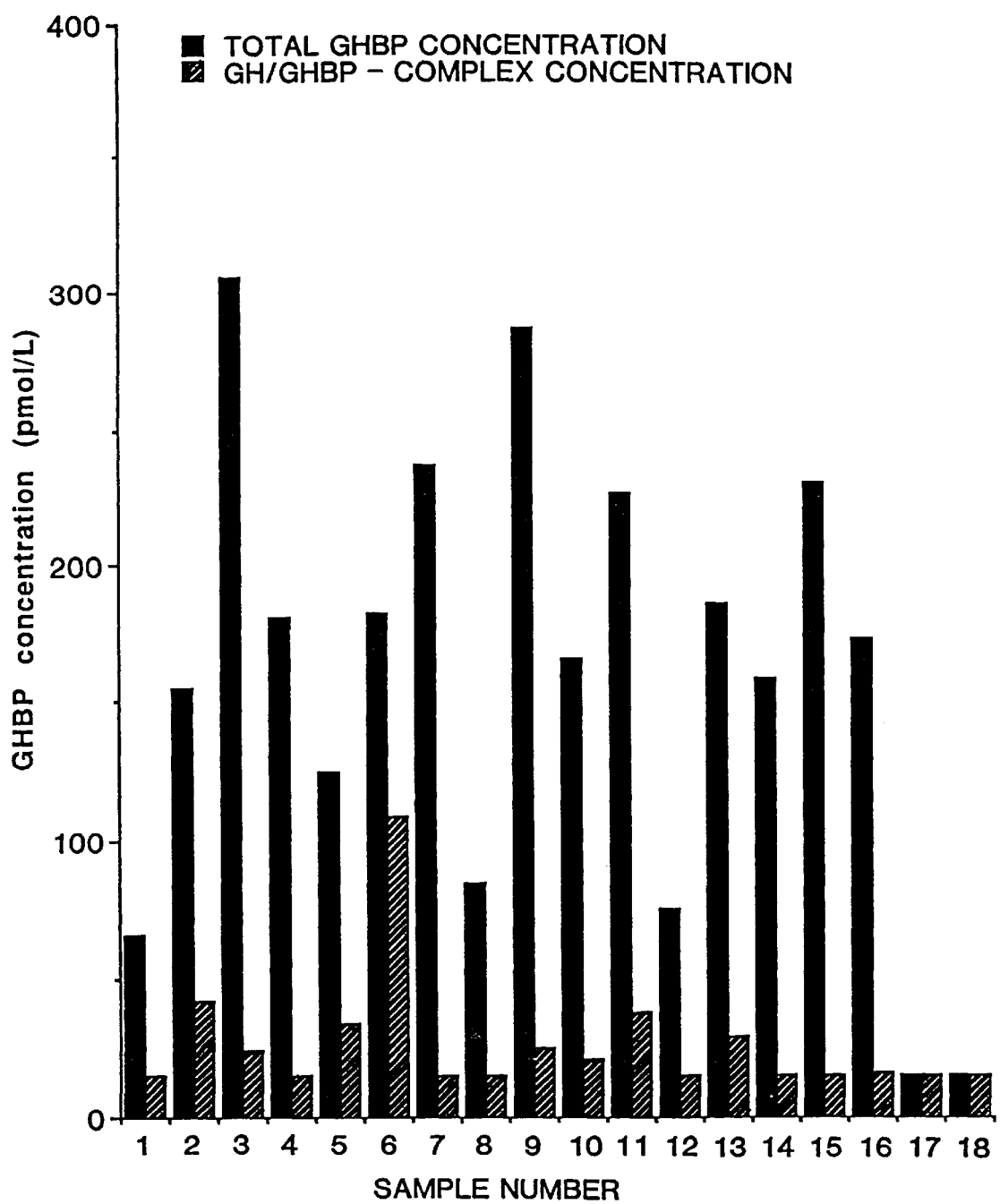
FIG. 6. Total- and hGH-bound-hGHBP levels in random serum samples from 16 healthy adults (sample #1–16) and two patients with Laron type dwarfism (sample #17 and 18).

In the sequential incubation experiment, 100 µL of GHBP (2.5 ng/100 µL) was allowed to react with immobilized MAb for 2 h, washed with wash buffer, and incubated for 4 h at room temperature with GH-I$^{125}$ (20,000 cpm/100 µL). The wells were washed 6 times in wash buffer, blotted thoroughly on adsorbent paper and counted in a LKB series 1277 gamma counter (Pharmacia LKB Nuclear Inc., Gaithersburg, Md.) for 1 minute (FIG. 6).

Simultaneous Assay n the simultaneous incubation experiment, 50 µL of GHBP at 2.5 ng/50 µL in incubation buffer and 50 µL of GH-I$^{125}$ at 20,000 cpm/50 µL in incubation buffer were incubated in each well for 4 h at room temperature. The wells were washed, blotted and counted as described above.

Preincubation Assay

In the pre-incubation experiment, 150 µL of GHBP at 2.5 ng/50 µL in incubation buffer and 150 µL of GH-I$^{125}$ at 20,000 cpm/50 µL in incubation buffer were incubated in test tube overnight at 4° C. The reaction mixture was then added (100 µL per well) to the MAb coated well and incubated for 4 h at room temperature. The wells were washed, blotted and counted as previously described.

Enzyme-conjugated Anti-hGH Antibodies

The anti-hGH detection MAb was selected for conjugation because it did not give detectable displacement of the GHBP and contains no overlapping determinants with the GHBP (Cunningham et al., Science 243:1330–1336 [1989]). The antibodies were purified from ascites fluid using protein A-Sepharose (Repligen Corp., Cambridge Mass.) following established procedures (Ey et al., Immunochem. 15:4239 [1978]: Goding, J. W., J. Immonol. Meth 20:241 [1978]) and stored sterile in 0.01M sodium phosphate, 0.15 M sodium chloride, pH 7.2 (PBS) at 4° C. Purified MAbs were conjugated to horseradish peroxidase (Nakane and Kawaoi, J. Histochem. Cytochem. 22:1084 [1974]) and stored at −20° C. in 50% glycerol.

LIFA assay standards

The recombinant human growth hormone binding protein (GHBP) was purified from a mammalian cell line following the procedure outlined by Spencer et al. (J. Biol. Chem. 263:7862–7867 [1988]). The purified GHBP amino acid composition as determined by quantitative amino acid analysis matched what was theoretically expected for the cloned gene product. The purified GHBP was homogeneous based on analysis of SDS-gel electrophoresis. The concentration of GHBP in the purified preparation was established by Scatchard analysis (Scatchard, G., Annals of the New York Academy of Sciences 51:660–672 [1949])., and dilutions of this sample in PBS containing per liter, 5 g of BSA, 5.0 mM EDTA, 0.5 ml of Tween 20 and 0.1 g of Thimerosal (assay buffer) were then used as standards in the LIFA. GHBP produced in E. coli was also used, but surprisingly found to give non-parallel dilution curves in the assay. Therefore, the preferred GHBP is either natural GHBP or GHBP produce by cells which produce GHBP in a native configuration, that is, glycosylated.

Recombinant human GH

Recombinant human growth hormone (GH) was supplied by Genentech Inc., South San Francisco, Calif., USA.

Serum and plasma samples

Serum and plasma (EDTA, citrate and heparin as anticoagulants) samples were obtained from healthy adult volunteers (9 men and 7 women, 26 to 43 years old). The samples were centrifuged and stored at −70° C. until assayed.

Therapeutic Treatment Following GHBP Evaluation

For the various proposes of this invention, the COMPOSITIONS (HGBP$_+$GH, GH, IGF-I, IGF-1+binding protein) administered to the mammal or avian by any suitable technique, including parenterally, and can be administered locally or systemically.

The COMPOSITIONS are directly administered to the mammal by any suitable technique, including parenterally, intranasally, or orally. The specific route of administration will depend, e.g., on the medical history of the patient, including any perceived or anticipated side or reduced anabolic effects using hGH or IGF-I alone, and the growth defect to be corrected. Examples of parenteral administration include subcutaneous, intramuscular, intravenous, intraarterial, and intraparitoneal administration. Most preferably, the administration is by continuous infusion (using, e.g., minipumps such as osmotic pumps), or by injection using, e.g., intravenous or subcutaneous means. Preferably, the COMPOSITIONS administration is subcutaneous. The administration may also be as a single bolus or by slow-release depot formulation. Most preferably, the IGF-I or IGF-1 plus binding protein is administered continuously by infusion, most preferably subcutaneously; GHBP+GH or GH alone is administered daily subcutaneously by injection. Most preferably, the GHBP+GH is administered intermittently every 2 or more days, weekly, biweekly, or monthly.

The IGF-I is suitably administered together with its binding protein, for example, BP53, which is described in WO 89/09268 published OCT. 5, 1989 and by Martin and Baxter, J. Biol. Chem., 261:8754–8760 (1986), the disclosures of which are incorporated herein by reference. This protein is an acid-stable component of about 53 Kd on a non-reducing SDS-PAGE gel of a 125–150 Kd glycoprotein complex found in human plasma that carries most of the endogenous IGFs and is also regulated by GH. The IGF-I is also suitably coupled to a receptor or antibody or antibody fragment for administration. Similarly, the GH can be delivered coupled to another agent such as an antibody, an antibody fragment, or one of its binding proteins.

The COMPOSITIONS to be used in the therapy will be formulated and dosed in a fashion consistent with good medical practice, taking into account the clinical condition of the individual patient (especially the side effects of treatment with hGH or IGF-I alone or growth retardation after continuous GH treatment), the site of delivery of the COMPOSITIONS, the method of administration, the scheduling of administration, and other factors know to practitioners. The "effective amounts" of each component for purposes herein are thus determined by such considerations and must be amounts that enhance the anbolic growth of the treated patient.

As a general proposition, the total pharmaceutically effective amount of each of the COMPOSITIONS administered parenterally per dose will be in the range of about 1 μg/kg/day to 50 mg/kg/day of patient body weight, although, as noted above, this will be subject to a great deal of therapeutic discretion. More preferably, this dose is at least 2 μg/kg/day, and most preferably at least 5 μg/kg/day for each hormone. If given continuously, the IGF-I, IGF-1+ binding protein, GHBP=GH and GH are each typically administered at a dose rate of about 1 μg/kg/hour to about 100 μg/kg/hour, either by 1–4 injections per day or by continuous subcutaneous infusions, for example, using a minipump. An intravenous bag solution may also be employed. The key factor in selecting an appropriate dose is the anabolic result obtained, as measured by increases in body weight gain, lean body mass, or statutory growth approximating the normal range, or by other criteria for measuring anabolic activity as defined herein as are deemed appropriate by the practitioner.

The COMPOSITIONS are also suitably administered by sustained-release system. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (U. Sidman et al., Biopolymers, 22, 547–556 (1983)), poly(2-hydroxyethyl methacrylate) (R. Langer et al., J. Biomed. Mater. Res., 15:167–277 (1981), and R. Langer, Chem. Tech., 12:98–105 (1982)), ethylene vinyl acetate (R. Langer et al., Id.) or poly-D- (-)-3-hdyroxybutyric acid (EP 133, 988). Sustained-release compositions also include liposomally entrapped COMPOSITIONS. Liposomes containing COMPOSITIONS are prepared by methods known per se: DE 3,218,121; Epstein et al., Proc. Natl. Acad. Sci. U.S.A., 82:3688–3621 (1985); Hwang et al., Proc. Natl. Acad. Sci. U.S.A., 77:4030–4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal COMPOSITIONS therapy.

For parenteral administration, in one embodiment, the IGF-I and GH are formulated generally by mixing each at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the COMPOSITIONS each uniformly and intimately with liquid carriers of finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine,; monosaccharides, disaccharides, and other carbohydrates including cellulose or its derivatives, glucose, mannose, or dextrins; chelating agents such as EDTA: sugar alcohols such as mannitol or sorbitol; counterions such as sodium, and/or nonionic surfactants such as polysorbates, poloxamers, or PEG.

The COMPOSITIONS are each typically formulated individually in such vehicles at a concentration of about 0.1 mg/ml t 100 mg/ml, preferably 1–10 mg/ml, at a pH of about 4.5 to 8. Full-length IGF- I is generally stable at a pH of no more than about 6; des(1–3)- IGF-I is stable at about 3.2 to 5; hGH and GHBP are stable at a higher pH of, e.g., 6.0–7.8. It will be understood that the use of certain of the foregoing excipients, carriers, or stabilizers will result in the formation of IGF-I or GH salts.

In addition, the COMPOSITIONS preferably the full-length IGF- I, are suitably formulated together in a suitable carrier vehicle to form a pharmaceutical composition that does not contain cells. In one embodiment, the buffer used for formulation will depend on whether the composition will be employed immediately upon mixing or stored for later use. If employed immediately after mixing, the COMPOSITIONS can be formulated in mannitol, glycine, and phosphate, pH 7.4. If this mixture is to be stored, it is formulated in a buffer at a pH of about 6, such as citrate, with a surfactant that increases the solubility of the GH at this pH, such as 0.1% polysorbate 20 or poloxamer 188. The final preparation may be a stable liquid or lyophilized solid.

The COMPOSITIONS to be used for therapeutic administration must be sterile. Sterility is readily accomplished by filtration through sterile filtration membranes (e.g., 0.2 micron membranes). Therapeutic COMPOSITIONS (IGF-I, IGF-1+binding protein, GHBP+GH and GH compositions) generally are placed into a container having a sterile access port, for example, an intravenous solution bag or vial having a stopper pierceable by a hypodermic injection needle.

COMPOSITIONS ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous GH solution, and the resulting mixture is lyophilized. The infusion solution is prepared by reconstituting the lyophilized GH using bacteriostatic Water-for-Injection.

GHBP plus GH ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous IGF-I solution, and the resulting mixture is lyophilized. The infusion solution is prepared by reconstituting the lyophilized GHBP plus GH using bacteriostatic Water-for-Injection. The GHBP+GH formulation may further contain mannitol, glycine, a buffer, and a non-ionic surfactant. The formulation of the subject invention may optionally include one of several types of non-ionic surfactants, such as the polysorbates (e.g. polysorbate 20, 80, etc.) and the poloxamers (e.g., poloxamer 188). When polysorbate 80 is used the molar ratio of GHBP+GH:polysorbate 80 is 1:0.07–30, advantageously 1:0.1–10, and most advantageously 1:3. On a weight to volume basis, polysorbate 80 is added in amounts of about 0.001 to about 2% (w/v), in order to enhance further the stability of the hGH. Polysorbate 80, in concentrations above 0.01% (w/v) reduces the amount of aggregation forming upon lyophilization. In addition to improved shell life, the surfactant containing formulation of the subject invention inhibits the formation of protein aggregates when the reconstituted formulation is shaken.

When GHBP+GH is administered, it must contain one or more of its binding proteins. A well characterized such binding protein is the high-affinity growth hormone bind protein (GHBP) constituting the extracellular domain of the GH receptor that circulates in blood and functions as a GHBP in several species [Ymer and Herington, Mol. Cell. Endocrino., 41:153 (1985); Smith and Talamantes, Endocrinology, 123:1489–1494 (1988); Emtner and Roos, Acta Endocrinologica (Copenh.), 122:296–302 (1990)], including man (Baumannn et al., J. Clin. Endocrinol. Metab., 62:134–141 (1986); EP 366,710 published May 9, 1990; Herington et al., J. Clin. Invest., 77:1817–1823 (1986); Leung et al., Nature, 330:537–543 (1987)). A second BP with lower affinity for GH has also been described that appears to be structurally unrelated to the GH receptor (Baumann and Shaw, J. Clin. Endocrinol. Metab., 70:680–686 (1990)).

Novel formulations of zinc, GHBP and GH result in a stable composition suitable for prolonged storage, and for therapeutic administration. Therapeutic formulations containing the $Zn^{2+}$ion are stable allowing therapeutic administration of the formulation. The formulation aspect of the present invention is thus directed to such formulation, and to all associated formulations and as a means for effectively stabilizing GHBP+GH. The formulation contains zinc, and substantially pure GHBP and GH free of contaminating proteins or infectious agents found in humans. Formulations of the present invention may additionally contain a pharmaceutically acceptable buffer, amino acid, bulking agent an/or non-ionic surfactant. These include, for example, buffers, chelating agents, antioxidants, preservatives, cosolvents, and the like; specific examples of these could include, trimethylamine salts ("Tris buffer"), and disodium edetate.

hGH Compositions

As used herein, the terms "human growth hormone" or "hGH" denote human growth hormone produced, for example, from natural source extraction and purification, and by recombinant cell culture systems. The native sequence of hGH and its characteristics are set forth, for example, in Hormone Drugs, Gueriguigan et al., U.S.P. Convention, Rockville, Md. (1982) The terms likewise cover biologically active human growth hormone equivalents; e.g., differing in one or more amino acid(s) in the overall sequence. Further, the terms as used in this application are intended to cover substitution, deletion and insertion amino acid variants of hGH, or post translational modificationsExamples of such variants are describe din PCT Pub. WO90/04788 published May 3, 1990. the hGH used in the formulations of the present invention is generally produced by recombinant means as previously discussed. The formulation of recombinant GHBP+GH is substantially pure, free of other human proteins, free of infectious agents such as the human immonodeficiency virus (HIV) and it is soluble. "Substantially pure" GHBP+GH means GHBP and GH that is free of proteins with which it ordinarily is associated in bodily fluids such as blood, plasma and serum. Ordinarily, substantially pure means GHBP and GH which is greater than about 95% pure by weight of total protein, and preferably greater than 98% pure by weight.

Formulation Amino acids

In an alternative formulation embodiment, a pharmaceutically acceptable amino acid, for example glycine, is added to the GHBP and GH:zinc ion formulation. When glycine is present, the molar ratio of GHBP+GH:glycine is 1:5–600 in addition to glycine, amino acids such as alanine, glutamine, asparagine, arginine or lysine or derivatives of such amino acids may be used in the subject formulation. Such amino acids are particularly advantageous when lyophilizing the formulation to create a sufficient mass to form a stable, dry caked formulation.

Non-Ionic Surfactant

In another embodiment a non-ionic surfactant is added to the GHBP+GH formulation. The formulation of the subject invention may optionally include one of several types of non-ionic surfactants, such as the polysorbates (e.G. polysorbate 20, 80 etc.) and the poloxamers (e.g. poloxamer 188). Advantageously polysorbate 80 is used, and the molar ratio of hGH:polysorbate 80 may be 1:0.03–60. On a weight to volume basis, polysorbate 80 is added in amounts of about 0.001 to about 2% (w/v), in order to enhance further the stability of the GHBP and GH. Polysorbate 80, in concentrations above 0.01% (w/v) may reduce the amount of inactive aggregates forming upon lyophilization and reconstitution. The use of non-ionic surfactants improves formulation stability when exposed to shear and surface stresses without causing denaturing of the protein. Further, such surfactant containing GHBP and GH formulations, may be employed in aerosol devices such as those used in a pulmonary dosing, and needless jet injector guns. Such delivery formulations may be improved by the addition of non-ionic surfactants in the range of 0.1–5% (w/v).

As used herein, the expression mammal refers to any mammal but especially primates, bovine, ovine, canine, feline, equine and rodentia. Specifically it includes human, cows, horses, rats, mice, rabbits, monkeys, cats, dogs and pigs. The term avain refers to any bird, particularly chicken, turkey, duck and goose.

The foregoing written specification is considered to be sufficient to enable one skilled in the art to practice the invention. The present invention is not to be limited in scope by the constructs deposited, since the deposited embodiment is intended to illustrate only certain aspects of the invention and any constructs that are functionally equivalent are within the scope of this invention. The deposit of material herein does not constitute an admission that the written description herein contained is inadequate to enable the practice of any aspect of the invention, including the best made thereof, nor is it to be construed as limiting the scope of the claims to the specific illustrations that they represent.

Indeed, various modifications of the invention in addition to those shown and described herein will become apparent to those skilled in the art from the foregoing description and fall within the scope of the appended claims. The following examples are intended to illustrate the best mode now known for practicing the invention, but the invention is not to be considered limited to these examples.

EXAMPLE 1

SELECTION OF GHBP ASSAY ANTIBODY

Two distinct antibodies are required for the LIFA method. The first antibody is a capture antibody which coats the solid phase and is used to selectively remove the GHBP from the biological sample being assayed. This antibody must be specific for epitopes which do not hinder the binding of the ligand hormone. The second detection antibody is specific for an epitope on the ligand hormone. This second detection antibody must bind the ligand hormone at a site that does not hinder its ability to complex with the HBP. In the case of GHBP, known commercially available monoclonal antibodies were screened for the desired binding properties. The detection monoclonal antibody specific for hGH was newly created in a mouse hybridoma system.

Coat MAb selection

Figure 2:
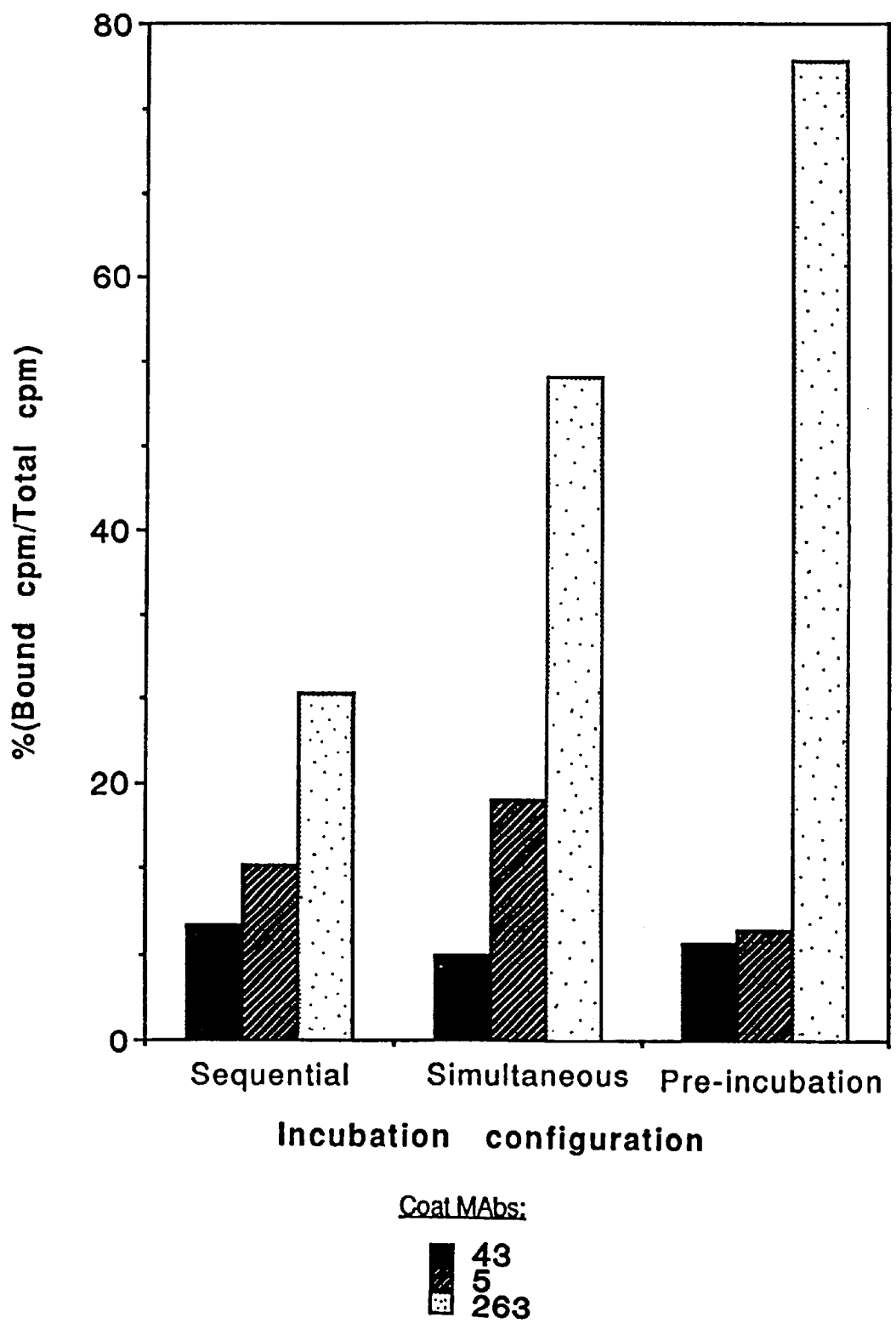
FIG. 2. Coal MAb selection, % bound GH-$I^{125}$ by MAb 5, 43 and 263 were ploted vs the three different incubation configurations. The immobilized MAbs were evaluated in three different experiments. In the first experiment, using sequential incubation steps, GHBP was first incubated with MAb coated on the well, followed by addition of radiolabelled GH (GH-$I^{125}$). In the second experiment the reaction of GHBP and GH-$I^{125}$ was carried out simultaneously in MAb coated wells. In the third experiment, GHBP was pre-incubated with hGH-$I^{125}$ overnight at 4° C. and then added to the MAb coated well.

For assaying for the presence of GHBP a capture antibody which binds GHBP is needed to coat the solid phase, in this case a microtiter plate well, for binding the HBP. Five mouse anti-GHBP MAbs (1, 5, 7, 43, and 263) were evaluated at their optimal coat concentration, first to determine their binding sites of GHBP relative to GHBP-GH i.e., sequential assay and their capacity to bind to GHBP in the presence of circulating GH-I$^{125}$ (simultaneous incubation format). They were then examined based on their capacity to bind to GHBP-GH-I$^{125}$ complex (pre-incubation experiment). Since both MAbs 1 and 7 show very weak binding in the sequential and simultaneous assay format, only MAbs 5, 43 and 263 were tested in the pre-incubation experiment. FIG. 2 shows the percent bound for each MAb under three different assay configuration. The data show that MAb 263, which gave the highest bound in all three conditions is the most suitable MAb as coat since it is able to bind to free GHBP as well a GHBP in complex with GH. More importantly, the sequential incubation experiment showed that the MAb 263 did not interfere with the present hGHBP-hGH binding site.

Figure 3:
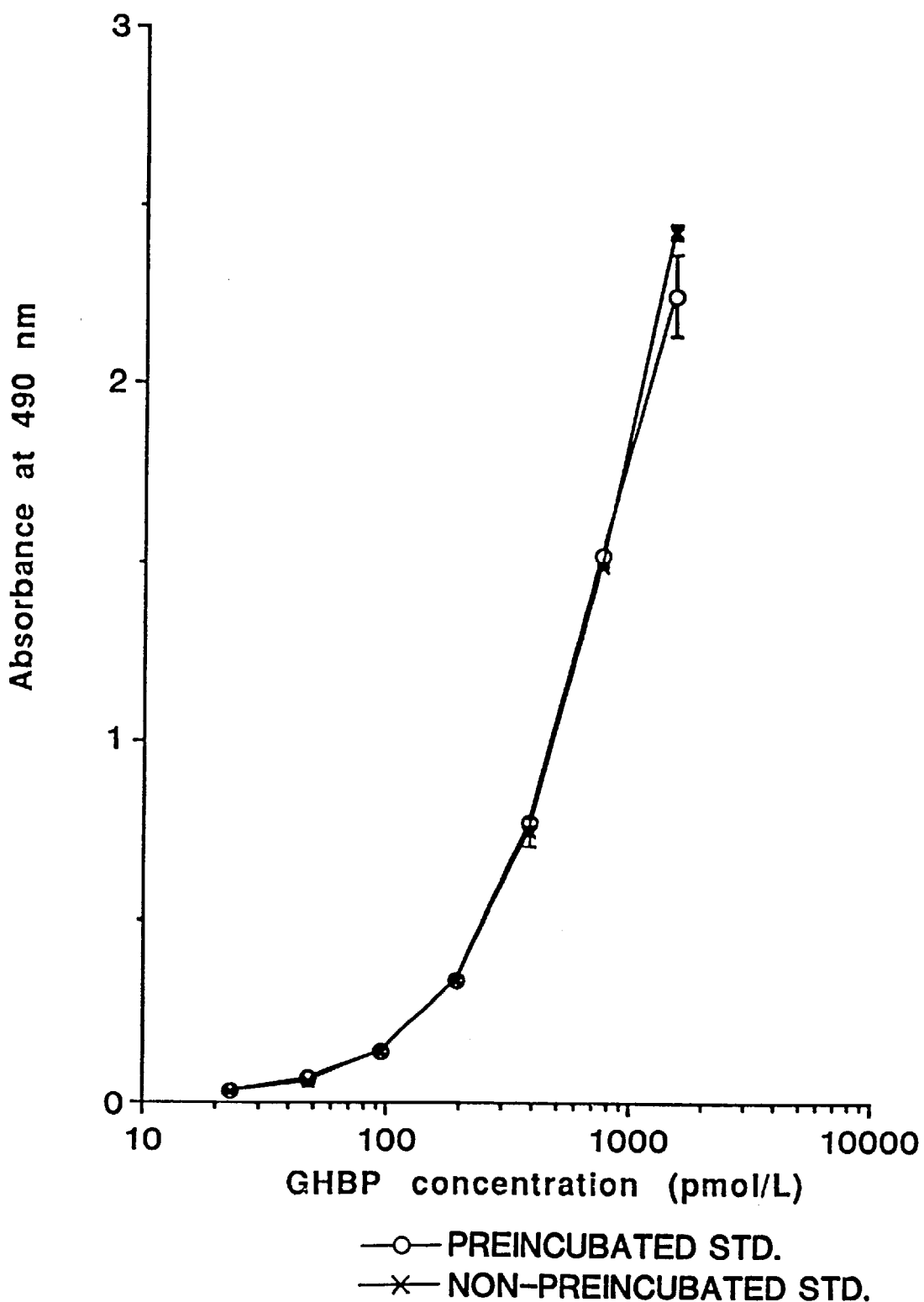
FIG. 3. Comparison of two standard curves generated with and without preincubation with GH. One set of standards were incubated with GH (final concentration 200 ng/ml) over night at +4° C. the control standards were incubated with assay buffer. The samples so generated were then assayed in the LIFA.

FIG. 3 shows a comparison of two standard curves generated with and without preincubation with hGH. One set of standards were incubated with hGH (final concentration 200 ng/ml) over night at 4° C., the control standards were incubated with assay buffer. The samples so generated were then assayed in the LIFA according to the standard protocol i.e. all samples were exposed to hGH on the microtiter plates. As seen in FIG. 3, similar results are obtained whether or not the GHBP is preincubated with hGH. The binding of the GHBP to the coat antibody and the saturation of the GHBP with its ligand can be carried out simultaneously by coincubating the samples and the hGH in the microtiter wells. The simplified LIFA gave a standard curve similar to that obtained with two separate steps but required only half the incubation time (2 h vs 4 h, FIG. 1, third box down).

Figure 4:
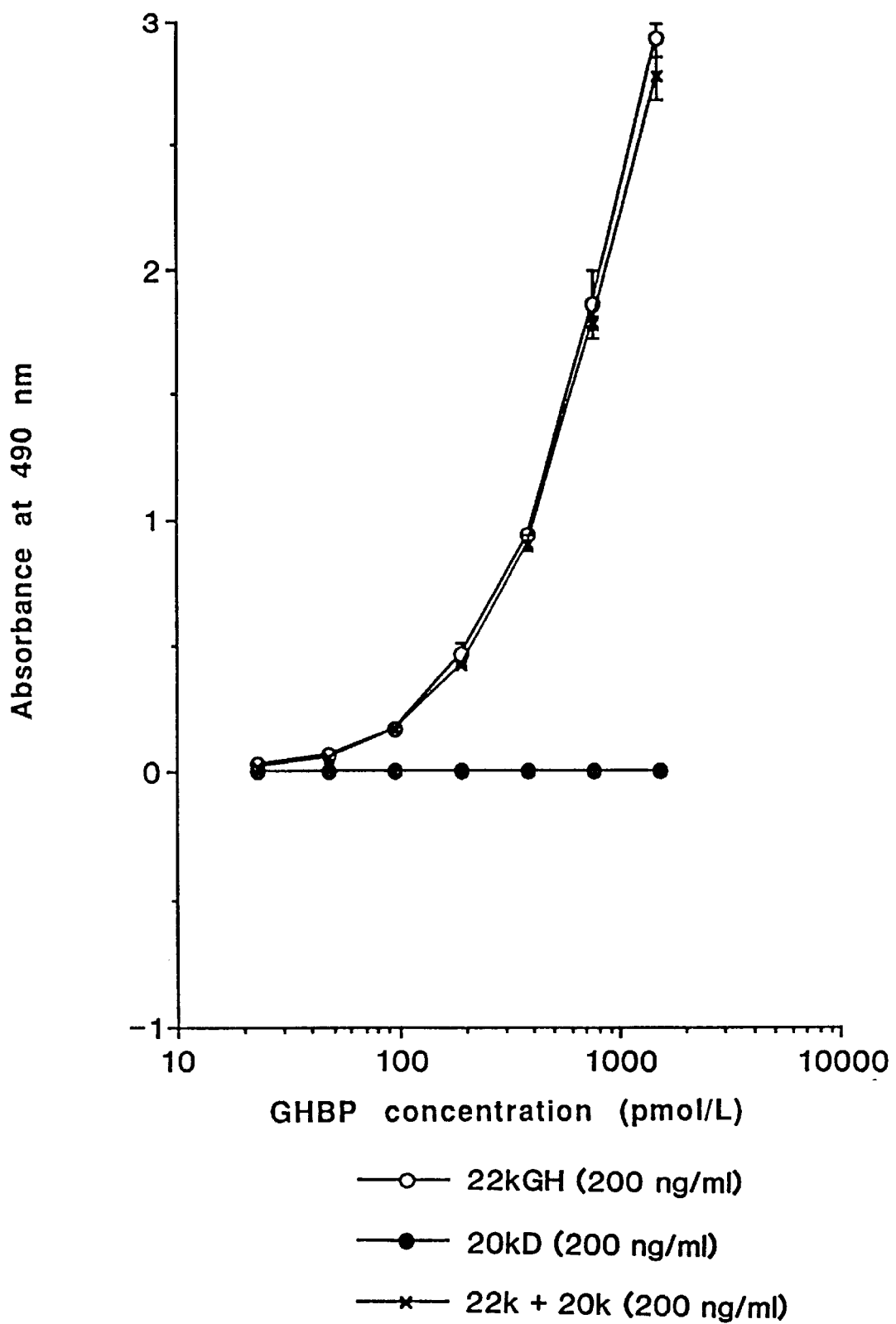
FIG. 4. Standard curves of hGHBP using 22 kD hGH as ligand, hGHBP using 20 kD as ligand, and hGHBP using a combination of hGH 22 kD and 20 kD.

The MCB, see below (Detection MAb Selection), which was used for HRPO-conjugation, binds to the 22 kDa-GH with high affinity, but has very low affinity for the 20 kDa and the possible interference by 20 kDa-GH in the assay was consequently tested. FIG. 4 shows that the addition of 200 ng/ml of the 20 kDa-hGH to the 200 ng/ml hGH solution results in a standard curve similar to that obtained by incubation with 200 ng/ml of hGH. This shows that the 20 kDa-GH does not interfere in the present GHBP assay to any substantial degree.

Detection MAb Selection

For assaying for the presence of hGH, a detection antibody is needed with high affinity for an epitope on the hGH which will not hinder the binding of the hGH to the GHBP. Monoclonal antibody was made in a mouse system using recombinant hGH and screened for the required specificity. The best mouse monoclonal antibody was produced by a hybridoma designated HGH-B. This hybridoma was deposited with the ATCC as previously discussed.

EXAMPLE 2

LIFA ASSAY PROCEDURE FOR GHBP

The LIFA assay procedure developed for measuring the GHBP is as follows. Ninety-six-well microtiter plates (Corning Glass Works, Corning, N.Y.) were coated with MAb 263 by incubating overnight at 4° C. with 100 μl/well of antibody at 20 μg/ml in 50 mmol/liter of sodium carbonate buffer, pH 9.6 (coat buffer) (see FIG. 1, step 1). After removal of the coating solution, the coated plates were blocked with 150 μl per well of 5 g/liter of BSA in PBS for 1 h at room temperature (FIG. 1, step 2), and washed six times with 0.5 g/liter of Tween 20 in PBS (wash buffer).

Standards diluted in assay buffer or samples (50 μM serum or plasma and 50 μM assay buffer) were dispensed onto the coated wells (100 μl/well) (FIG. 1, step 3). Plates were sealed and incubated at room temperature for 2 h with gentle agitation. Plates were washed six times with wash buffer. Recombinant hGH at 200 ng/ml or assay buffer was then added (100 μl/well) and incubated at room temperature for 2 h. Plates were washed six times with wash buffer before addition of horseradish peroxidase (HRPO) labelled MAb MCB (100 μl/well) FIG. 1, step 4). After further incubation for 2 h at room temperature, the plates were washed six times with wash buffer. Freshly prepared substrate solution (0.4 g of o-phenylenediamine dihydrochloride in one liter of PBS plus 0.4 ml of 30% hydrogen peroxide) was added to the plates (100 μl per well) and incubation carried out in the dark for 15 min at room temperature FIG. 1, step 5. The reaction was stopped by the addition of 100 μl of 2.25 mol/L sulfuric acid and absorbance at 490 nm determined on a Vmax plate reader (Molecular Devices, Menlo Park, Calif.). A standard curve was generated by plotting absorbance vs. log of GHBP concentration, using a 4-parameter nonlinear regression curve fitting program. Sample concentrations were obtained by interpolation of their absorbance on the standard curve.

EXAMPLE 3

PROPERTIES OF THE GHBP ASSAY

The GHBP assay was evaluated and the range, sensitivity, specificity, and precision of the assay determined.

The specificity of this assay was tested by substituting the GHBP with four other soluble receptors (rCD4, rHER2 ECD, EGF-receptor and rPRL-receptor) and an unrelated protein produced in CHO cells (HIV envelope protein, gp120). All four proteins were obtained from Genentech Inc. The results (Table 1) showed that the assay has less than 0.01% cross-reactivity with these proteins. In addition, cross-reactivity with human placental lactogen (HPL) and human prolactin (PRL) was tested. Substituting HPL and PRL for hGH at the same concentration (200 ng/ml) resulted in values undistinguishable from the blanks when when tested together with the GHBP or PRL-receptor.

TABLE 1

CROSS-REACTIVITY

| Protein Tested | Concentration Tested (μg/ml) | Measured (ng/ml)[b] | Cross-reactivity[a] % |
|---|---|---|---|
| rHER2 ECD | 10.0 | <0.06 | <0.01 |
| rCD4 | 10.0 | <0.06 | <0.01 |
| rgp120 | 10.0 | <0.06 | <0.01 |
| EGF-receptor | 10.0 | <0.06 | <0.01 |
| rPRL-receptor | 10.0 | <0.06 | <0.01 |

Assay precision

Serum samples with low, medium, or high GHBP concentrations were analyzed in 24 replicates for the assessment of intra-assay precision (Table IIA). Interassay precision was determined by measuring samples of low, medium or high GHBP concentrations in ten separate experiments (Table 2B). The coefficients of intra-assay variation at all three levels ranged from 6.3 to 8.9% while the coefficients of interassay variation ranged from 9.7 to 12.9%.

TABLE 2

PRECISION OF THE LIFA

|  | Sample 1 | Sample 2 | Sample 3 |
|---|---|---|---|
| A. Intra-assay Precision |  |  |  |
| Replicates | 24 | 24 | 24 |
| Mean (pmol/L) | 138 | 268 | 614 |
| S.D. (pmol/L) | 9.2 | 16.9 | 54.6 |
| C.V. (%) | 6.6 | 6.3 | 8.9 |
| B. Interassay Precision |  |  |  |
| Replicates | 10 | 10 | 10 |
| Mean (pmol/L) | 136 | 293 | 674 |
| S.D. (pmol/L) | 17.6 | 33.1 | 65.0 |
| C.V. (%) | 12.9 | 11.3 | 9.6 |

Linearity of the assay

Figure 5:
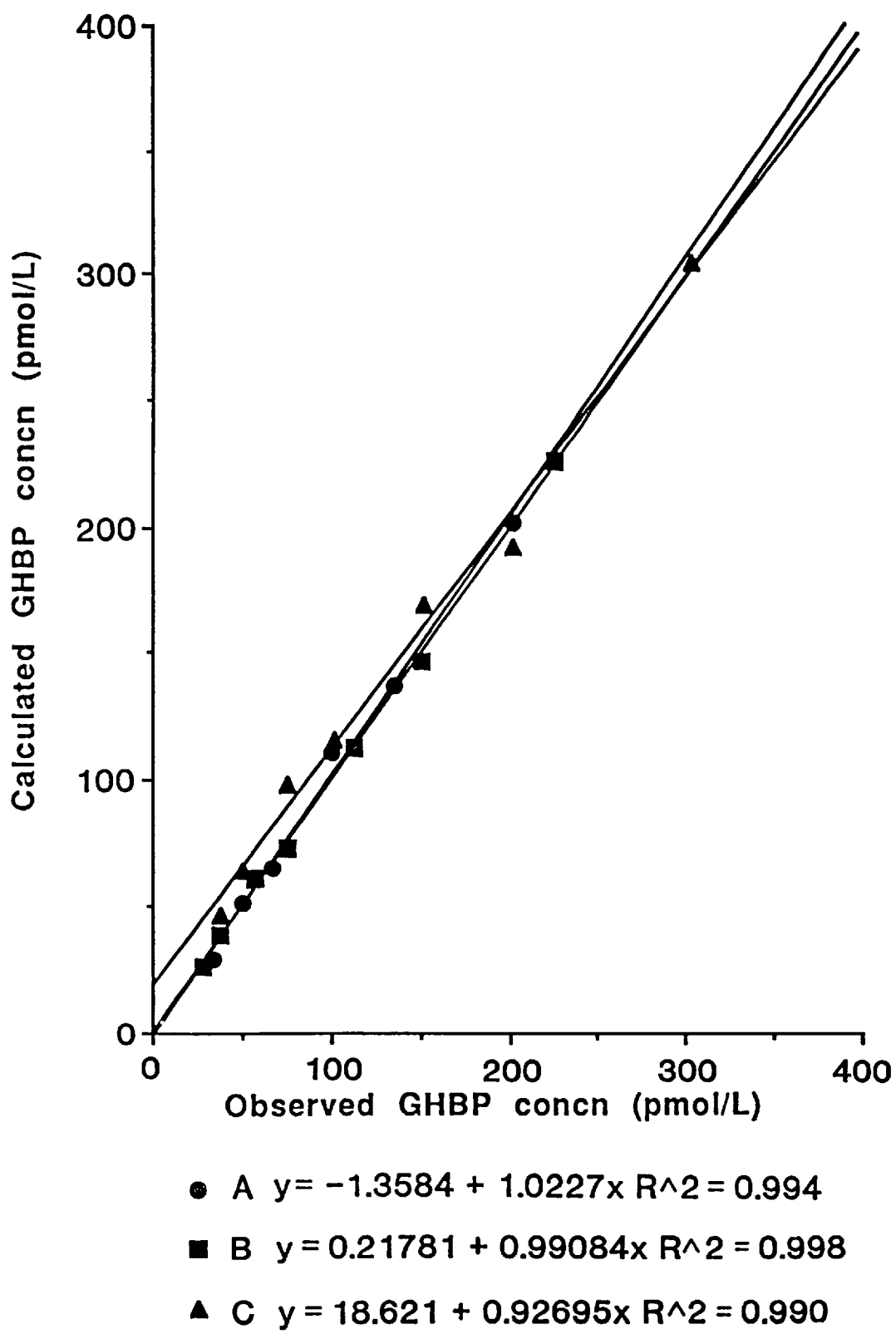
FIG. 5. Plot of theoretical hGHBP concentration based on dilution of three different serum samples vs. hGHBP concentration in the serum samples diluted in assay buffer and measured by LIFA.

The linearity of the assay was determined by making serial dilutions of serum sample sin assay buffer and measuring the concentration of GHBP. Results were examined by correlating the observed concentration determined in the LIFA with the calculated concentration obtained by multiplying the dilution factor with the concentration of the undiluted sample determined in the LIFA. Linear regression analysis of the samples resulted in correlation coefficients of 0.99 or greater (FIG. 5), indicating that the assay is linear.

EXAMPLE 4

DETERMINING GHBP IN BIOLOGICAL FLUIDS

Spike recovery

Purified GHBP at three different concentrations in assay buffer were added in equal volume to four serum samples and four plasma samples. The generated samples were assayed in the LIFA. The theoretical concentration was calculated for each mixed sample and was used to calculate percent recovery. The data in Table 3A and Table 3B show an average recovery of 106.7 and 99.5 for serum and plasma respectively, with a range of 89.1 to 115.9%, demonstrating the accuracy of the assay.

Saturation of the GH-BP with GH

FIG. 3 shows a comparison of two standard curves generated with and without preincubation with GH. One set of standards were incubated with GH (final concentration 200 ng/ml) overnight at 4° C., the control standards were incubated with assay buffer. The samples so generated were then assayed in the LIFA according to the standard protocol, i.e. all samples were exposed to GH on the microtiter plates. As seen in FIG. 2, similar results are obtained whether or not the GHBP is preincubated with GH.

Application of the LIFA method

Total and GH-bound GHBP levels in random serum samples from 16 healthy adults and two patients with Laron type dwarfism are shown in FIG. 6. GH-BP levels were detectable in samples from all normal subjects (FIG. 6; patients 1–16). In contrast, GHBP concentrations were undetectable (<30 pmol/L) in both patients with Laron-type dwarfism (FIG. 6: patients #17, #18).

TABLE 3A

ACCURACY[a] In serum

| Spiked Sample[b] (pmole/L) | Serum Sample[b] (pmole/L) | Expected[c] (pmole/L) | Observed (pmole/L) | % Recovery |
|---|---|---|---|---|
| 204 | 177 | 192 | 212 | 110.4 |
|  | 238 | 219 | 254 | 115.9 |
|  | 465 | 225 | 362 | 105.9 |
|  | 1138 | 671 | 735 | 109.5 |
| 658 | 177 | 419 | 412 | 97.6 |
|  | 238 | 446 | 500 | 111.1 |
|  | 465 | 562 | 577 | 101.8 |
|  | 1138 | 898 | 962 | 107.1 |
| 1427 | 177 | 802 | 762 | 95.0 |
|  | 238 | 832 | 931 | 112.0 |
|  | 465 | 946 | 965 | 102.1 |
|  | 1138 | 1282 | 1438 | 111.9 |
|  |  |  | Average | 106.7 |
|  |  |  | Range | 95.0–115.9 |

[a]Equal volumn of three purified rGHBP (column #1) were each added to serum samples (column #2) and assayed in the LIFA.
[b]GHBP concentrations had been determined previously by LIFA.
[c](spiked + serum)/2

TABLE 3B

ACCURACY[a] In plasma

| Spiked Sample[b] (pmole/L) | Plasma Sample[b] (pmole/L) | Expected[c] (pmole/L) | Observed (pmole/L) | % Recovery |
|---|---|---|---|---|
| 142 | 100 | 121 | 112 | 92.6 |
|  | 150 | 146 | 154 | 105.5 |
|  | 300 | 221 | 231 | 104.5 |
|  | 569 | 355 | 335 | 94.4 |
| 435 | 100 | 267 | 254 | 95.1 |
|  | 150 | 292 | 323 | 110.6 |
|  | 300 | 367 | 327 | 89.1 |
|  | 569 | 502 | 500 | 99.6 |
| 835 | 100 | 467 | 458 | 98.1 |
|  | 150 | 492 | 538 | 109.3 |
|  | 300 | 567 | 531 | 93.6 |
|  | 569 | 702 | 715 | 101.9 |
|  |  |  | Average | 99.5 |
|  |  |  | Range | 89.1–110.6 |

[a]Equal volumn of thred purified rGHBP (column #1) were each added to serum samples (column #2) and assayed in the LIFA.
[b]GHBP concentrations had been determined previously by LIFA.
[c](spiked + serum)/2

EXAMPLE 5

MONITORING OF GHBP IN GROWTH PROMOTION

The LIFA of the present invention may be used to monitor the concentration of GHBP in the biological fluids of a patient, and if the level is inadequate for the desired rate of growth, additional GHBP administered. An example of low GHBP levels is in Laron dwarfism; whereas a high GHBP levels may be present in patients with excess GH secretion. If the level GHBP is insufficient for the desired rate of growth, additional GHBP alone or complexed to hGH may be administered. The optimal level of GHBP may be determined by the methods discussed above, in combination with measuring the level of GHBP in a series of normal healthy individuals. GHBP may be evaluated in any mammalian system, preferably in rodents and primates.

In Rodents

Two rodent models of GH deficiency are used: 1) rats where the gland producing GH, the pituitary, is surgically removed (hypophy-sectomized rats) and 2) animals genetically deficient in growth hormone (dwarf rats, Charlton, H. W. et al., J. Endo. 119:51–58 [1988]). These rats are tested with human GH (hGH) along or hGH coupled to human GHBP which is produced recombinantly in $E.$ $coli$ or alternatively in mammalian 293 cells. Several indices of growth are measured to assess the effect of the binding protein on GH-induced body growth. Monitoring of the level of GHBP and GH is required to determine the metabolic fate of administered GHBP and complexed GH.

Hypophysectomized Rats

Recombinant hGHBP and hGH are given either alone or in combination to hypophysectomized rats, a recognized model for measuring GH bioactivity (Thorngren, K-G. & Hansson L. I. Acta. Endo. 75:653–668 [1977]). Human GH (0.03, 0.1 and 0.3 mg/kg, as 7 daily injections) induces a dose-related weight gain while injections of $E.$ $coli$-derived hGHBP at these same 3 doses produces no effect by itself. However, co-administration of 0.3 mg/kg hGHBP with 0.1 mg/kg hGH not only gives greater weight gain than 0.1 mg/kg hGH alone (p<0.01), but also induces greater weight gain than three times more hGH ($22.0 \pm 3.6$ vs $17.1 \pm 2.1$ g respectively; mean$\pm$s.d., p<0.01). Longitudinal bone growth parallels body weight gain. Thus, co-administration of 0.3 mg/kg hGHBP and 0.1 mg/kg hGH gives greater bone growth than 0.3 mg/kg hGH ($102 \pm 14$ vs $84 \pm 17$ microns/day; p<0.05), and 0.1 mg/kg hGHBP plus hGH gives greater bone growth than hGH alone ($99 \pm 6$ vs $72 \pm 1$) microns/day; p<0.01).

The liver, spleen and kidney are all significantly larger following co-administration of hGHBP (0.3 mg/kg) with hGH (0.1 mg/kg) than with 0.1 mg/kg hGH alone: liver ($5.5 \pm 0.4$ vs $4.6 \pm 0.6$ g; p<0.01), spleen($292_{35}$ 44 vs $240 \pm 34$ mg; p<0.05), and kidney ($836 \pm 60$ vs $716 \pm 57$ mg; p<0.05). The weights of liver, spleen and kidney in excipient treated rats are $4.5 \pm 0.2$ g, $193 \pm 32$ mg, and $687 \pm 58$ mg, respectively. These responses to hGH are at least doubled by hGHBP. The serum concentrations of IGF-1 and hGH 24 h after the last injection are markedly elevated by co-administration of the two highest doses of hGHBP with hGH, while hGHBP causes as much as 20-fold more hGH to be present after 24 h.

An ELISA (Fuh, G. et al., J. Biol. Chem. 265:3111–3115 [1990]) for hGHBP adapted for use in serum shows the reason for the persistence of the GH in the blood 24 hours after the seventh subcutaneous bolus injection was given to the rats. The hGHBP is only detectable in the animals co-administered hGHBP and hGH. When the GHBP is given alone it disappears from the blood more rapidly than when the GHBP is given complexed to GH. These findings form measuring the GHBP in blood suggest that it is the persistence of the GH+GHBP complex in the blood of the rats that causes many or all of the above improved activities of GH. The LIFA method of the present invention is therefore used to follow GHBP during its preparation, storage, use and in body fluids following GHBP administration.

Dwarf Rat System

We also compared hGH and hGHBP in a dwarf rat which has a pituitary GH content 5–10% of normal, grows slowly, and responds to GH treatment (Charlton, H. W. et al., J. Endo. 119:51–58 [1988]) Co-administration of 0.27 mg/kg of hGHBP with 0.27 mg/kg hGH increases weight gain compared to 0.27 mg/kg hGH alone ($11.1_{\pm}4.2$ vs $7.5_{\pm}1.7$ g; p<0.05). Co-administration of all three doses of hGHBP with 0.27 mg/kg of hGH significantly increasing bone growth compared to 0.27 mg/kg hGH alone (low $33.5_{\pm}5.8$, medium $38.6_{\pm}8.6$, high $35.5_{\pm}5.0$ vs $26.0_{\pm}4.1$ microns/day; p<0.05). Serum IGF-1 concentrations are elevated by co-administration even compared to 0.81 mg/kg hGH alone (high hGHBP $136_{\pm}45$ vs $90_{\pm}16$ ng per ml; p<0.05) as were hGH concentrations (high hGHBP, $609_{\pm}240$ vs $73_{\pm}22$ pg per ml; p<0.0001).

GHBP from Mammalian 293 Cells n market contrast, hGHBP produced in human 293 cells completely inhibits GH responses in hypophysectomized rats. Weight gains after 10 daily s.c. injections of hGH alone are $11.3_{\pm}2.5$, $16.4_{\pm}2.1$ and $21.1_{\pm}2.1$ g at 0.03, 0.1, and 0.3 mg/kg/day respectively. When hGH at 0.03 and 0.1 mg/kg/day is co administered with a 2-fold molar excess of 293-derived hGHBP this weight gain is abolished ($3.0_{\pm}2.1$ and $3.0_{\pm}1.6$ g, respectively) compared to the hGH and excipients ($2.3_{\pm}1.6$ g) groups. This difference between the growth responses induced using these 2 forms of hGHBP may be due to a difference in hGH clearance from the circulation which is reduced about 10 fold for GHBP derived from *E. coli* (Moore, J. A. et al, Proc. US Endocr. Soc. 71, Abstract #1652 [1989]).or purified from natural sources (Baumann, G. & Shaw, M. A., J. Clin Endocrinol. Metab., 70:680–686 [1990];Baumann, G., Shaw, M. A. & Buchanan, T. A., Metabolism. 38:330–333 [1989].

The clearance (ml/min/kg) of hGH in normal male rats, following an i.v. bolus of hGH alone is $18.6_{\pm}3.4$, for hGH co-administered with GMBP from rabbit sera is $2.1_{\pm}0.2$, for GHBP from *E. coli* $1.9_{\pm}0.4$, or from 293 cells $41.3_{\pm}16.7$. Therefore, for the 293-derived hGHBP the clearance of hGH is increased two fold, suggesting a correlation between in vivo potency and hGH clearance. The decreased clearance of hGH complexed to the *E. coli*-derived hGHBP maybe due to the complex being of sufficient size (Mr>40 kDa) to escape filtration by the kidney. Proteins produced in 293 cells can have heterogenous carbohydrate patterns, possible due to incomplete glycosylation, causing them to be rapidly cleared by the liver, which may explain the rapid clearance of 293-derived hGHBP.

In this instance the 293-derived GHBP therefore acts as an inhibitor of GH action, compared to the enhancing activities of the *E. coli*-derived protein. This difference in activity appears to be due to the differing clearances of the two molecules from the blood. The present invention aids in similarly discriminating inhibitory and stimulatory binding proteins on the basis of their clearance from the blood.

Persistence of GHBP

This series of experiments shows the value of the knowledge gained from a GHBP assay, and naturally follows from the above rat experiments. On the basis of the prolonged half-life of the *E. coli*-derived GH plus GHBP complex in blood, the GHBP allows GH to persist in the blood for sufficient time to allow less frequent GH injections when the GH is coupled to GHBP.

In 2 separate studies we inject hGH by itself, or combined and co-injected with hGHBP, in GH deficient dwarf rats. In the first study hGH or hGH plus hGHBP are given daily or every 2 or 4 days for 8 days. The second study is designed so that hGH or hGH plus hGHBP are given daily or every 3 or 6 days for 18 days. In both studies hGHBP gives greater growth responses than hGH alone no matter the injection interval. These studies show that when hGH is injected with hGHBP the injection frequency can be greatly reduced, to one or twice a week, without reducing the size of the growth response.

Female dwarf rats (Study A, 12–15 weeks of age, 110–130 g; Study B, 50–70 days of age, 95–110 g) are randomized into groups of 8 (Study A) or 7 (Study B), and injected i.p. with tetracycline as an intravital marker of bone growth. All injections of GH or GHBP are given subcutaneously in a volume of 100 microlitres of solution. In each study, all rats are given a daily injection of either excipients or test compounds and weighed daily.

The hGH used is rhGH (Genentech Lot N9267AX, G042A) dissolved in sterile water. The GHBP used is produced in *E. coli* and purified. In this case the GHBP has an altered sequence to the GHBP used above, the molecule being produced by removing the exon 3 coding domain giving a 1–5, 27–238, peptide sequence.

In the first experiment the hGH and hGHBP are prepared to be injected in a volume of 0.1 ml as:
  a) hGH 0.25 mg/ml or
  b) hGH 1 mg/ml
  c) hGH 1 mg/ml)+hGHBP (2 mg/ml)
The 8 regimes of injection are:
  1) Daily injections of a), b), and c),
  2) Injections every 2 days of b) and c)
  3) Injections every 4 days of b) and c)
  4) Injections of excipient every day.
Therefore in this design the animals injected s.c. every 2nd day receive only half the GH dose of the animals given daily injections and the rats injected every 4the day receive only a quarter of the cumulative GH dose.

In the second experiment the hGH is prepared as:
  a) 0.33 mg/ml,
  b) 1 mg/ml, or
  c) 2 mg/ml.
The hGH+hGHBP solutions are 0.33, 1 or 2 mg/ml of hGH combined with 2-fold more hGHBP (0.66, 2 or 4 mg/ml, respectively), The 9 regimes all injected in 0.1 ml s.c. are:
  1) Excipient control
  2) Daily hGH injections 33 micrograms/day
  3) Daily hGH injections 100 micrograms/day
  4) Daily hGH injections 33 micrograms/day+66 µg of GHBP
  5) Daily hGH injections 100 micrograms/day+200 µg of GHBP
  6) Every 3rd day hGH injections 100 micrograms/shot
  7) Every 6th day hGH injections 200 micrograms/shot
  8) Every 3rd day injections 100 micrograms hGH+200 µg GHBP/shot
  9) Every 6th day injections 200 micrograms hGH+400 µg GHBP/shot Therefore, in this design the animals injected s.c. every 3rd or 6th day receive the same cumulative GH dose (0.33 mg/kg/day) as those injected s.c. with the low dose of GH.

The response to hGH is increased at all frequencies of injection by combining hGHBP with the hGH. It is surprising that in study A despite decreasing the injection frequency from daily to every 2 days, and thereby reducing the cumulative hGH dose by half, the weight gain response GHBP+GH injections is the same. For hGH injections the weight gain response is markedly reduced when the injections are given every 2 or 4 days. The weight gain in response to eight daily injections of 0.25 mg/kg hGH is identical to that for only 2 injections of the same cumulative dose of hGH given every 4 days.

In the second Experiment, two doses of hGH are given daily with or without a 2-fold excess of hGHBP. The response to hGH is greatly increased by combining hGHBP with the hGH (see below). (In a subsequent study in the dwarf rat the maximal weight gain response to hGH was increased when the hGH was complex with and injected daily s.c. with hGHBP.) As in the previous experiments GHBP improved the IGF-1 response to the GH. This appears to be due to the GHBP-GH complex causing a preferential and disproportionate growth of the liver, an activity lacking when GH is delivered alone. Giving the same total dose of hGH at 3 or 6 day intervals gives a poor growth response (compared to hGH given daily, Group 2). The weight gain response to combined treatment with GH+GHBP is much greater. The effect of daily hGH alone is directly compared with hGH+hGHBP given every 3 or 6 days. Infrequent injections of the hGHBP-hGH combination are as effective as daily injections of hGH. These data clearly show that the co-administration of hGH+hGHBP allows the growth response to the hGH to be maintained with infrequent injection regimes. Co-administration of GH+GHBP allows the interval between injections to be extended to 6 days (weekly) without a loss of activity on longitudinal bone growth (measured by the tetracycline labelling technique) compared to injections of the same dose of GH injected daily. The co-administration of GH+GHBP also allows a smaller dose of GH to be given less frequently for an equivalent growth response (injections every 2 or 3 days at ½ to ⅓ the dose in the rat).

STUDY B: Bone Growth and Weight Gain in 18 days

| Group | Bone Growth (microns) & SD | | Weight Gain (g) & SD | |
|---|---|---|---|---|
| 1) Excipient | 34.0 | 8.0 | 10.3 | 3.6 |
| 2) low GH | 53.8 | 8.3 | 27.8 | 3.3 |
| 3) Hi GH | 62.1 | 8.4 | 34.0 | 5.4 |
| 4) Low GH + GHBP | 73.4 | 9.7 | 28.1 | 4.9 |
| 5) Hi GH + GHBP | 95.1 | 6.5 | 47.0 | 7.4 |
| 6) GH/3 days | 37.7 | 10.3 | 15.2 | 3.7 |
| 7) GH/6 days | 36.5 | 11.7 | 16.8 | 6.2 |
| 8) GH + GHBP/3 days | 56.9 | 15.8 | 28.0 | 6.4 |
| 9) GH + GHBP/6 days | 47.0 | 4.6 | 18.5 | 4.8 |

In Primates

In normal juvenile Rhesus monkeys GHBP was monitored after administration of GHBP+hGH or after hGH alone. The somatogenic and anabolic response was determined by measuring IGF-1 concentrations. The monkeys received either hGH daily or hGHBP+hGH weekly, and there was an excipient injected control group. The results, primarily from blood IGF-1 concentrations, showed that GHBP enhances the biologically activity of GH in primates. The dose of hGH (administered with twice the molar ratio of hGHBP) was 0.35 mg/kg injected weekly, the doses of hGH injected daily were 0.05 mg/kg or 0.35 mg/kg. Serum analyses indicated that the maximum IGF-1 response to hGH+hGHBP is greater than for hGH alone at either dosage. As measured, the hGH serum life when administered in combination with hGHBP was increased 2.2 times over that of hGH administered alone. The administration of 0.35 mg/kg hGH daily stimulated serum IGF-1 less than a single weekly administration of hGH (0.35 mg/kg) complexed with hGHBP at a 2:1 molar ratio. Weekly administration of hGH+hGHBP (1:2 molar ratio, given subcutaneously as a bolus), resulted in a physiological response greater than daily hGH administration of the same hGH dose, or a seven-fold greater total dose. Therefore, lesser amounts of hGH can be administered and less frequent injections given if hGH is complexed with hGHBP. In summary, in the rat and in the monkey, GHBP enhances GH activity, so that in humans a similar enhancement is expected.

The mechanism of the above effects of the GHBP on body growth could be explained by the greatly delayed absorption of the GH-GHBP complex from s.c. injections and then the delayed clearance from the blood of the GH-GHBP complex. Both these effects are demonstrated. The magnitude of this effect is quite surprising as the absorption of free GHBP was similar to that for GH alone. These pharmacokinetic mechanisms explain a large part of the increased activity, and the ability to give less frequent injections of the GHBP+GH complex. These discoveries are surprising as there is no prior art showing that increasing the half-life of GH in the blood would inevitably lead to an increased activity. If a molecule is retained in the blood its access to tissues will be limited, yet degradation of the molecule in the blood will continue. If the GH is bound to the GHBP access of the GH to a cellular GH receptor would be expected to be modified. It is clear that for the molecule to be active on tissues it must pass from the bloodstream into the tissues, so that there are limits to the degree of delayed clearance that is desirable.

EXAMPLE 6

Analysis of 24-Hour Plasma Profiles of GHBP, GH/GH-GHBP-Complex and GH in Healthy Children We have used the LIFA to measure GHBP levels in plasma profiles from healthy children. GH was measured by IRMA. Fifteen 24 h plasma profiles from 12 healthy children (3 girls and 9 boys) of different ages (6–17 years), heights (−3.7 to +3.5 SDS) and pubertal stages (1 to 4) were examined. Blood was withdrawn continuously for 24 h and collected in 20 min fractions. Time series for GH, GHBP and GH/GHBP-complex were analyzed by cross-correlation and Fourier analysis. GH was secreted in a pulsatile fashion in all subjects. The concentration of the GH/GHBP-complex varied during the sampling period, and the changes correlated significantly with the GH pulses with correlation coefficients reaching maximum at zero time lag. In contrast, the changes in the total GHBP concentration were minor (CV-10%), and not correlated to GH pulses. Fourier analysis showed similar spectral power patterns for GH and GH/GHBP-complex, suggesting a diurnal rhythm (12–24 h periods) as well as components of higher frequencies (around 4 h periods). In spite of the subtle fluctuations in the total GHBP concentration, Fourier transformation revealed a marked diurnal rhythm, while components of higher frequencies were much less abundant. We conclude that the variations in total GHBP during a 24 h sampling period are small and that the levels can be estimated from a single random blood sample.

Materials and Methods

Subjects

Twelve children, 3 girls and 9 boys, of different ages (6–15 years old), heights (−3.7 to +3.5 SDS) and pubertal stages (stage 1–4), were investigated at the Children's Hospital, Göteborg, Sweden. Two of the subjects were studied on more than one occasion (Table 4). Height at the time of the study was expressed in SD scores compared to normal Swedish children (Karlberg P, Taranger J, Engström I, Lichtenstein H, Svennberg-Redegren I. The somatic development of children in a Swedish urban community. Acta Pediatrica Scand. 1976; Suppl. 258:1). All children were healthy and well nourished, and had normal thyroid, liver and kidney function. Coeliac disease was excluded. Children with classical GH deficiency were not included in the study. The testicular volume was measured by orchidometer, and the pubertal stages were classified according to Tanner (Tanner J M, Whitehouse R H. Clinical longitudinal standards for height velocity, weight velocity and stages of puberty. (Arch. Dis. Child. 51:170–179 [1976]).

TABLE 4

SUBJECT CHARACTERISTICS

| Profile No | Subject | Sex | Age | Height (SDS) | Weight (SDS) | Puberty B/T[a] | PH[b] |
|---|---|---|---|---|---|---|---|
| 1 | A | Female | 6 0/12 | +2.5 | +2.0 | 1 | 1 |
| 2 | B | Female | 12 8/12 | −1.9 | −2.0 | 1 | 1 |
| 3 | C | Female | 13 3/12 | −1.0 | 0 | 3 | 2 |
| 4 | D | Male | 7 11/12 | −0.3 | +0.5 | 1 ml | 1 |
| 5 | E | Male | 11 0/12 | −2.3 | −2.0 | 2 ml | 1 |
| 6 | F | Male | 11 2/12 | −2.0 | −1.5 | 3 ml | 1 |
| 7 | G | Male | 11 3/12 | +3.0 | +2 | 2 ml | 1 |
| 8 | H | Male | 13 0/12 | +1.0 | +1.0 | 15 ml | 3 |
| 9 | H | Male | 13 9/12 | +0.8 | +0.8 | 15 ml | 4 |
| 10 | I | Male | 12 5/12 | +0.7 | +0.1 | 4 ml | 1 |
| 11 | I | Male | 12 6/12 | +0.7 | 0 | 4 ml | 1 |
| 12 | I | Male | 13 3/12 | +0.4 | −0.4 | 5 ml | 1 |
| 13 | J | Male | 14 0/12 | −1.8 | −1.8 | 6 ml | 1 |
| 14 | K | Male | 14 7/12 | −2.5 | −1.5 | 12 ml | 3 |
| 15 | L | Male | 14 8/12 | −3.7 | −3.2 | 5 ml | 2 |

[a]Breast development (B), testicular volume (T).
[b]Pubic hair (PH).

Study Protocol

The Children stayed at the hospital for at least 2 days. They were given a normal diet, with breakfast at 08.00 h, lunch at 12.00 h, dinner at 17.00 h, and were allowed normal activity and sleep. A heparinized needle (Carmeda, Stockholm, Sweden) was inserted on the first evening. The following morning, at 08.00 h–09.00 h, blood withdrawal began through a thrombogenic catheter (Carmeda) inserted through the needle and connected to a constant withdrawal pump (Swemed A B, Göteborg, Sweden). The rate of withdrawal was 0.5–2 ml/h and the volume of the tubing was 0.1–0.2 ml. The heparinized reservoir tubes were changed every 20 min for 24 h, thus giving 72 samples. The blood samples were kept at room temperature and centrifuged within 24 h. After centrifugation the plasma was frozen until assayed.

GH Measurements

Plasma GH concentration was determined in duplicate using a polyclonal antibody-based IRMA (Pharmacia, Sweden) and the WHO First International Reference Preparation hGH 66217 as standard. Intra-assay variation was 3.2 to 3.5% at GH levels between 2–100 mU/L. Interassay variation was 5.0% and 2.7% at GH concentrations of 10 mU/L and 40 mU/L, respectively. When appropriate, a conversion factor of 2.7 U/mg, and a molecular weight of 22 000 was used to express GH concentrations in pmol/L.

GHBP Measurements

Total GHBP was measured by LIFA as previously discussed in detail. Briefly, ninety-six-well microtiter plates (Corning Glass Works, Corning, N.Y.) were coated with a monoclonal antibody directed against GHBP (MAb 263, Agen, Australia) by incubating overnight at 4° C. with 100 $\mu$L/well of antibody at 10 $\mu$g/mL in coat buffer. The coated wells were blocked and washed. Standards (recombinant hGHBP, Genentech Inc.) or samples (50 $\mu$L per well) were dispensed into the coated wells containing 50 $\mu$l/well of 200 ng/ml rhGH. Plates were sealed, incubated at room temperature for 2 h with gentle agitation, then washed before addition of a monoclonal anti-hGH antibody (MAb MCB, Genentech Inc) conjugated to horseradish peroxidase (100 $\mu$l/well). After further incubation for 2 h at room temperature, the plates were washed six times with wash buffer. Freshly prepared substrate solution (0.4 g of o-phenylenediamine dihydrochloride in one liter of PBS plus 0.4 mL of 30% hydrogen peroxide) was added to the plates (100 $\mu$l per well) and the incubation carried out in the dark for 15 min at room temperature. The reaction was stopped by the addition of 100 $\mu$l of 2.25 mol/L sulfuric acid and the absorbance at 490 nm determined. The same procedure, without the addition of rhGH to the samples, was used to measure the plasma concentration of the GH/GHBP-complex. The detection range in the LIFA was 15.6 to 1000 pmol/L. The intra- and interassay coefficients of variation were 7.3% and 11.3%, respectively.

Statistical Analysis

The rhythmicity of the 24 h profiles was analyzed by Fourier transformation. The original GH, GHBP and GH/GHBP-complex concentration time series were smoothed with a 3-point moving average (weights $w_{-1} = w_{+1} = \frac{1}{4}$, $w_0 = \frac{1}{2}$) in order to reduce the influence of high frequency components. The smoothed series were analyzed as Fourier expansions(Chatfield C. The analysis of time series, Chapman and Hall, London, 1989). The results are expressed as a power spectrum, where the amplitude is plotted as a function of frequency. To analyze the data for correlations between GH, GHBP and GH/GHBP-complex, cross-correlation followed by Box-Jenkins autoregressive modeling (Haugh L. Box GEP. Identification of dynamic regression (distributed lag) models connecting two time series. Journal of the American Statistics Association, 1977; 72:121–130) was used.

RESULTS

Plasma Profiles of GH GH/GHBP-Complex and Total GHBP

Figure 7B:
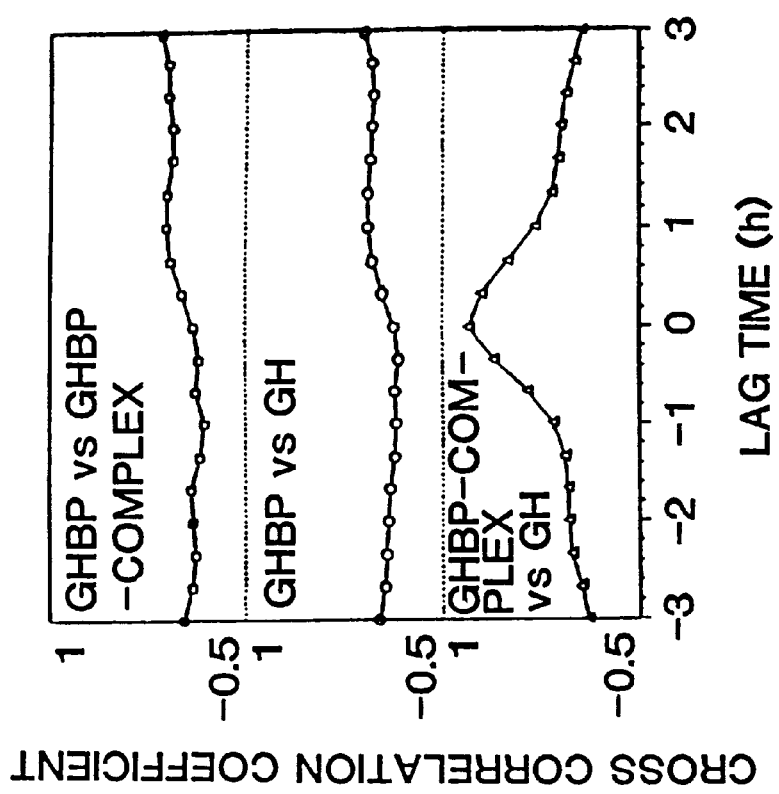
FIGS. 7(A–B). Cross correlation of GH and GHBP (A) Twenty-four hour plasma profiles of GH (top panel), GH/GHBP-complex (middle panel) and total GHBP concentration (bottom panel) in samples from a a 15 year old body (profile No. 15, Table 4); (B) statistical cross correlation analysis of data from (A).
Figure 7A:
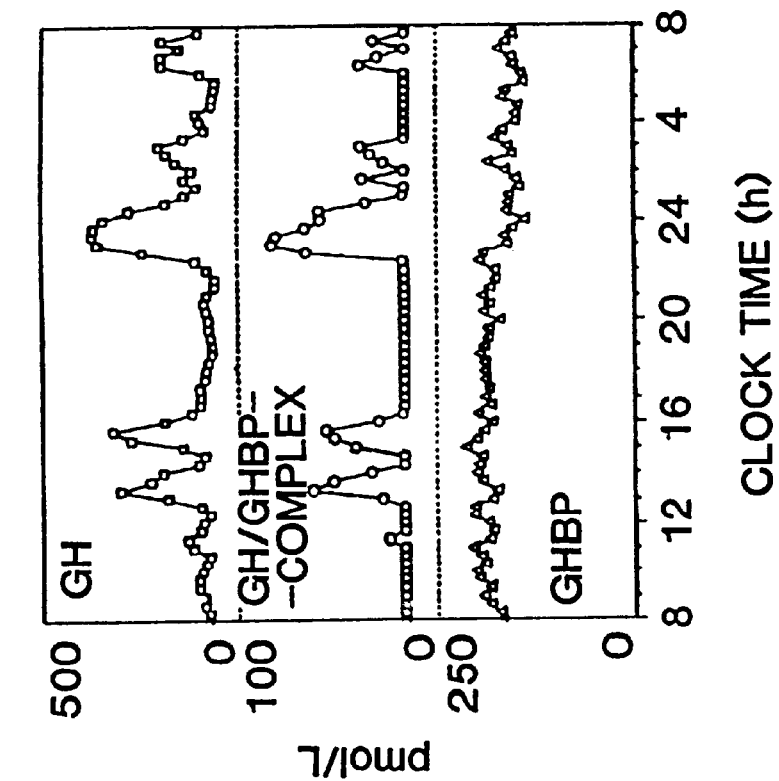
Figure 8A:
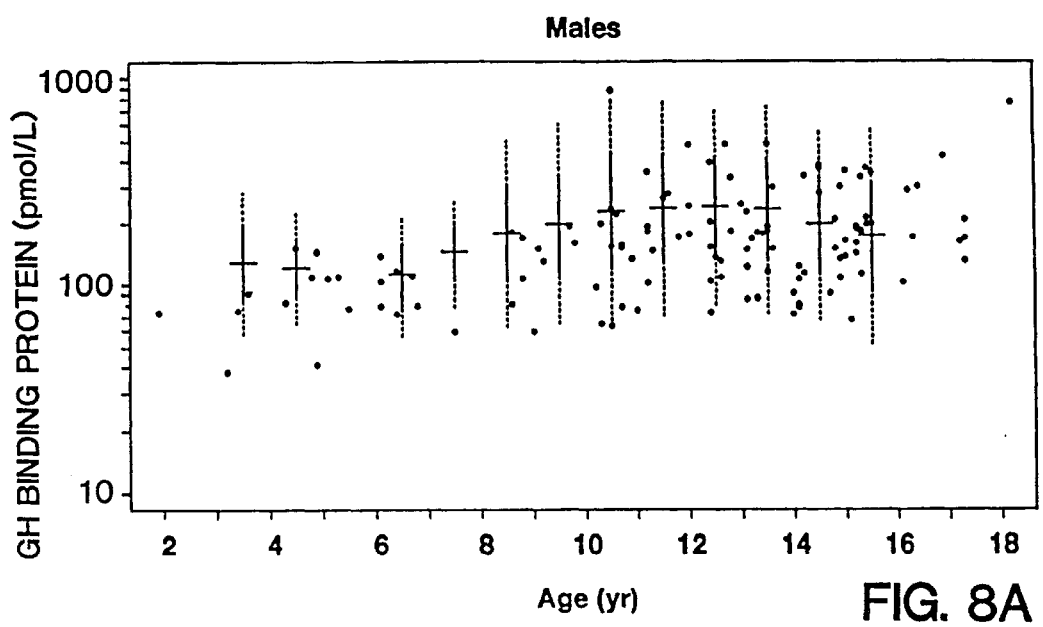
FIGS. 8(A–E) GH binding protein levels in National Cooperative Growth Study (NCGS) patients indicating the log concentration of GHBP vs the age of patient. The crossbars represent mean values; solid vertical lines are plus or minus 1 SDs; dotted vertical lines are plus or minus two standard deviations (SDs). The separate black dots each represent one patient. (A) idiopathic growth hormone deficiency (GHD) for mates; (B) idiopathic GHD for females; (C) Idiopathic short stature (ISS) for mates; (D) ISS for females; (E) Turner Syndrome.
Figure 8B:
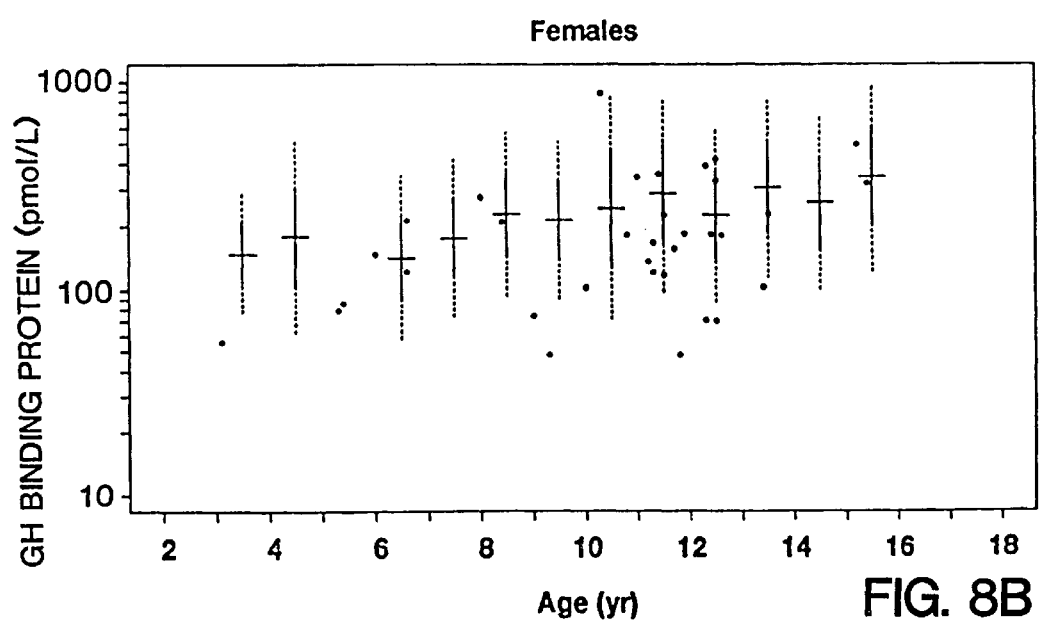
Figure 8C:
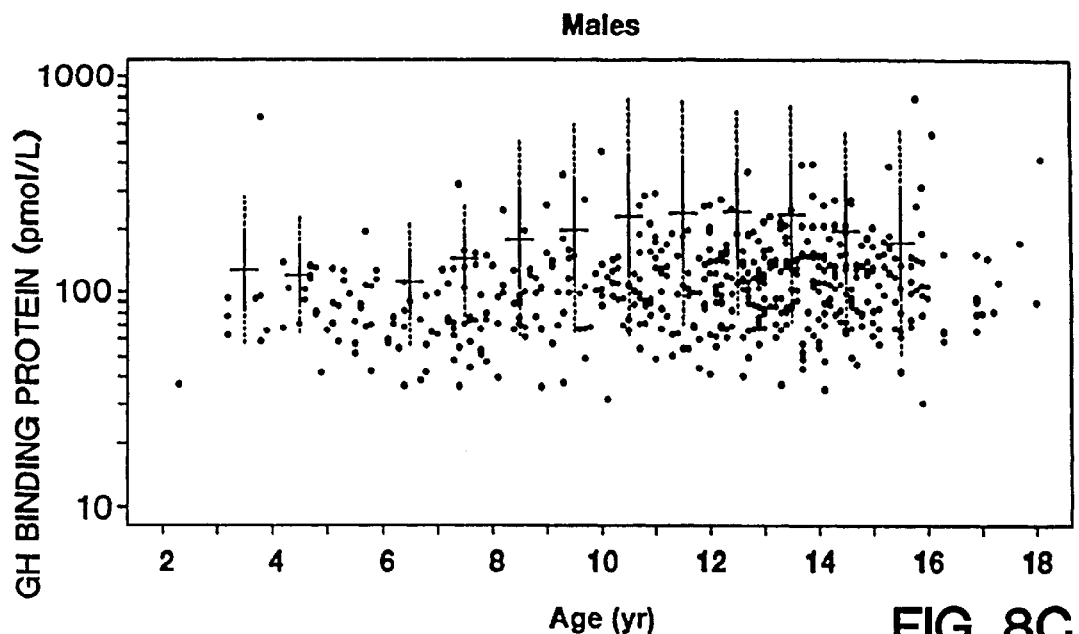
Figure 8D:
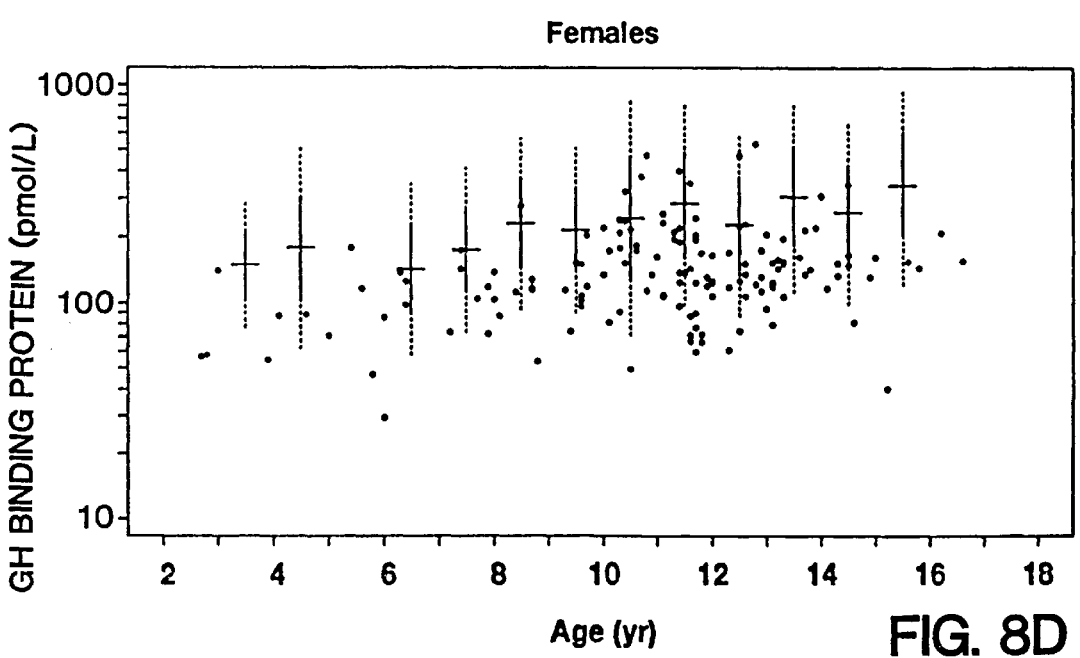
Figure 8E:
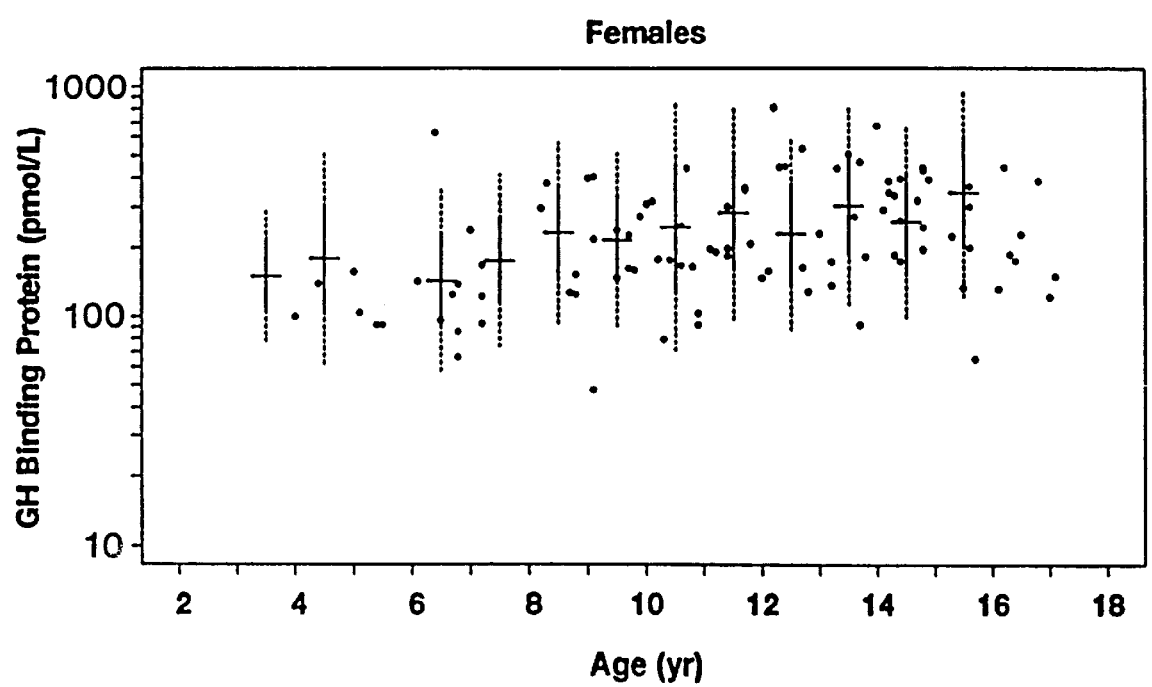

Twenty-four hour plasma profiles of GH, GH/GHBP-complex and total GHBP from one representative subject (profile #15) are shown in FIG. 7. Plasma concentrations of both GH (top panel) and GH/GHBP-complex (middle panel) varied over a wide range during the sampling period, and the changes appeared to be synchronized in time. In contrast, the total concentration of GHBP (lower panel) was much less variable, and did not seem to be influenced by the changes in GH and GH/GHBP-complex concentration.

Plasma Concentrations of GH, GHBP and GH/GHBP-Complex

Plasma concentrations of GH, GHBP and GH/GHBP-complex are shown in Table 5. The values given are the mean and coefficients of variation (CV) for each individual 24 h profile as well as the group average. The mean concentration of GHBP, GH/GHBP-complex and GH varied among different individuals (range 109–247 pmol/L, 13–109 pmol/L and 32–215 pmol/L for GHBP, GH/GHBP-complex and GH, respectively). The highly pulsatile nature of GH and GH/GHBP-complex plasma profiles were reflected in their high CV (156.0% and 47.2%, respectively). The percentage of GH that was bound to GHBP in high GH peaks (250 pmol/L) was 14.6%. The concentration of total GHBP was much less variable during the sampling period, as illustrated by the low coefficient of variation (9.6%) (Table 5). The complete 24 h profiles of total GHBP concentration from all subjects illustrated that levels vary among individuals and that the concentration for each subject is relatively constant throughout the day.

capture antibody, so the GH/GHBP-complex that is measured in the LIFA is the heterodimer formed by one GH molecule and one GHBP molecule. When GH concentration increases, (e.g. when rhGH is added to the sample in the LIFA or during endogenous GH peaks), the trimer [GH-(GHBP)2] dissociates and dimers [GH-GHBP] are formed, which can be bound by the MAb 263. This implies that all the GHBP, including GHBP molecules in endogenously formed trimers, are detectable in the assay for the total GHBP concentration.

We found that about 15% of GH in high peaks (>250 pmol/L) appear to be bound in the GH/GHBP-complex, but

TABLE 5

Mean plasma concentration of total GHBP, GH/GHBP-complex and GH.

| Profile No. | Total Mean (pmol/L) | GHBP CV (%) | GH/GHBP -complex Mean (pmol/L) | CV (%) | GH Mean (pmol/L) | P CV (%) |
|---|---|---|---|---|---|---|
| 1 | 109.3 | 9.4 | 34.8 | 25.6 | 73.1 | 129.6 |
| 2 | 235.2 | 9.5 | 12.9 | 113.9 | 83.3 | 178.5 |
| 3 | 179.0 | 12.7 | 26.2 | 111.0 | 99.8 | 128.9 |
| 4 | 148.5 | 8.1 | 24.1 | 25.8 | 40.4 | 107.7 |
| 5 | 198.9 | 7.8 | 47.3 | 51.0 | 167.9 | 176.7 |
| 6 | 160.1 | 8.6 | 25.7 | 28.6 | 36.6 | 160.7 |
| 7 | 215.0 | 5.5 | 39.8 | 22.5 | 31.6 | 151.0 |
| 8 | 247.4 | 7.7 | 108.8 | 15.3 | 215.2 | 121.6 |
| 9 | 217.5 | 9.3 | 80.1 | 17.2 | 189.1 | 133.7 |
| 10 | 126.2 | 11.8 | 28.2 | 46.4 | 163.4 | 151.3 |
| 11 | 120.4 | 13.8 | 20.7 | 37.0 | 101.9 | 125.7 |
| 12 | 168.7 | 9.2 | 34.3 | 43.4 | 99.8 | 119.4 |
| 13 | 130.0 | 11.1 | 29.5 | 41.5 | 140.9 | 154.9 |
| 14 | 191.1 | 11.8 | 19.8 | 107.5 | 103.7 | 99.1 |
| 15 | 199.8 | 7.0 | 45.4 | 21.9 | 39.3 | 153.5 |
| Mean: | 176.5 | 9.6 ± 0.6 | 38.5 | 47.2 ± 9.2 | 110.0 | 139 ± 6.3 |

Discussion

The objective in monitoring GHBP was to investigate the possible diurnal variations in the plasma concentration of GHBP in healthy children, and to determine if fluctuations in GHBP concentrations were correlated with the episodic release of GH. The subjects included in our study differed in age, sex, pubertal stage, height and GH levels. From a practical point of view we believe that a most useful discovery from the data is that total GHBP concentration shows only minor variations during a 24 h sampling period, implying that a single blood sample should give a good estimation of the total GHBP level. Nevertheless, rigorous analysis of the data revealed that the small (CV-10%) fluctuations in total GHBP plasma concentration account for a significant circadian rhythm. No significant cross-correlation between GH pulses and changes in total GHBP concentration was found. In contrast, the plasma concentration of GH/GHBP-complex showed rapid fluctuations, which were highly correlated with the changes in GH concentration. Fourier analysis showed that the plasma patterns of both GH and GH/GHBP-complex follow a diurnal rhythm but also possess components of higher frequencies (around 4 h periods).

The described LIFA, which was used for the GHBP measurements has the advantages that only functional GHBP is detected and that endogenous GH, which fluctuates rapidly over a wide range, does not affect the measurement of total GHBP concentrations. The assay can also measure the concentration of the GH/GHBP-complex. It was recently reported that when the ratio of GHBP to GH exceeds 1:1, trimers can form consisting of one GH molecule and two GHBP molecules. The trimer can not be bound by the the total bound fraction of GH may be higher since some GH may have formed trimers with the GHBP.

The variation in the plasma concentration of GHBP in serial samples has previously been addressed in two studies (Snow, K J, Shaw M A, Winer L M, Baumann G. Diurnal pattern of plasma growth hormone-binding protein in man. J Clin Endocrinol Metab. 70:417–420 (1990); Hochberg Z, Amit T, Zadik Z. Twenty-four-hour profile of plasma growth hormone-binding protein. J. Clin Endocrinol Metab. 72:236–239 (1991)). The study by Snow et al., which was carried out in adults with low GH levels, agrees with out results that there is no major variation in total GHBP levels during the sampling period. However, since GH pulses were absent or very low in the study by Snow et al., the possibility that there could be GH induced variation in GHBP levels in subjects with pulsatile GH secretion could not be excluded. In another study, by Hochberg et al., GH and GHBP levels were measured in samples obtained from normal children with pulsatile GH secretion and it was concluded that within 30 min the majority of the GH pulses were accompanied by GHBP pulses. This is in contrast to the present results, where only minor changes in the total GHBP concentration were detected and they were not correlated with the GH pulses. The reason for the discrepancy between the two studies is not clear, but may be due to differences between the GHBP assays. The LIFA directly measures total GHBP (i.e. the sum of free GHBP and GH-bound GHBP), while the assay used by Hochberg et al. is based on the binding of radiolabeled hGH to the GHBP and the values are then corrected for interference by endogenous GH. Since our data regarding the GH/GHBP-complex indicate that the complex is formed and cleared rapidly, it is possible that the apparent GHBP pulses, which Hochberg et al observed 30 min after a GH pulse may reflect the desaturation of the GHBP, thereby allowing more labeled GH to be bound.

The total GHBP levels varied over a wide range in different subjects (109–247 pmol/L) and it is probably that these levels are correlated to differences in age, sex, pubertal stage, growth velocity, etc. We conclude that GHBP levels are relatively constant throughout the day and a single or pooled blood sample should be sufficient to estimate total GHBP concentration. This finding should facilitate comparisons with larger populations and illustrates the value of GHBP measurement as a diagnostic tool.

EXAMPLE 7

GHBP DETERMINATIONS OF NORMAL AND SHORT STATURE CHILDREN

Growth hormone binding protein was assayed using the LIFA assay for human GHBP. The results are described in Tables 6, 7, 8 and 9 below. These tables contain summary statistics on GHBP levels in normal children (Table 6) as well as in children with short stature due to three different etiologies: idiopathic growth hormone deficiency (GHD) (Table 7), (ISS) (Table 8) and Turner syndrome (Table 9). Normal data were obtained from samples in Genentech's control and from collaborations with outside investigators. The samples from children with short stature were obtained as part of an ongoing post-marketing surveillance project from Protropin® human growth hormone, the Genentech National Cooperative Growth Study (NCGS). Now ISS children are now longer ideopathic in that the GHBP deficiency likely reflects an underlying growth hormone receptor deficiency.

The summary statistics for normal children are presented by sex and age and represent our best estimate of a normal range for GHBP. These statistics consist of the mean and mean plus or minus 2 standard deviations (SD) and were determined from the logged (base 10) values of the GHBP levels, then converted back to the original units. Sample sizes used in the estimates are included with the summary statistics. Note that there were sufficient data to perform these calculations for male and female children aged, 3, 4 and 6 through 15 only. Data from children of other ages and from adults were too sparse to allow a good estimate of the mean.

The summary statistics listed for each of the etiologies of short stature are the sample size, means and means plus or minus one SD. These values were computed in the same manner as that described for the normals. The statistics are printed by age and sex for all available data regardless of sample size. The units of GHBP are in pmole/liter.

TABLE 6

Growth Hormone Binding Protein Norms (GHBP Normal Range)

| Sex | Age | N | Mean − 2 SD | Mean | Mean + 2 SD |
|---|---|---|---|---|---|
| Male | 3 | 20 | 57.4 | 127.3 | 282.5 |
| Male | 4 | 21 | 64.6 | 120.2 | 223.5 |
| Male | 6 | 31 | 56.5 | 111.6 | 220.6 |
| Male | 7 | 31 | 78.2 | 143.0 | 261.7 |
| Male | 8 | 34 | 62.7 | 178.5 | 507.7 |
| Male | 9 | 36 | 64.9 | 198.1 | 604.7 |
| Male | 10 | 37 | 62.5 | 226.9 | 822.8 |
| Male | 11 | 40 | 70.7 | 234.6 | 779.0 |

TABLE 6-continued

Growth Hormone Binding Protein Norms (GHBP Normal Range)

| Sex | Age | N | Mean − 2 SD | Mean | Mean + 2 SD |
|---|---|---|---|---|---|
| Male | 12 | 48 | 79.4 | 238.0 | 713.3 |
| Male | 13 | 33 | 72.5 | 231.7 | 739.9 |
| Male | 14 | 37 | 67.6 | 97.7 | 578.4 |
| Male | 15 | 33 | 51.7 | 173.4 | 581.8 |
| Female | 3 | 15 | 77.4 | 149.3 | 288.0 |
| Female | 4 | 17 | 62.0 | 179.3 | 518.6 |
| Female | 6 | 33 | 57.8 | 142.7 | 351.9 |
| Female | 7 | 32 | 73.5 | 175.2 | 417.7 |
| Female | 8 | 33 | 93.7 | 230.9 | 568.8 |
| Female | 9 | 36 | 90.8 | 215.7 | 512.4 |
| Female | 10 | 32 | 71.2 | 244.6 | 841.0 |
| Female | 11 | 33 | 97.5 | 285.8 | 838.3 |
| Female | 12 | 36 | 87.7 | 228.7 | 596.8 |
| Female | 13 | 36 | 113.0 | 305.9 | 827.8 |
| Female | 14 | 35 | 99.7 | 260.2 | 678.7 |
| Female | 15 | 28 | 122.4 | 345.8 | 976.5 |

TABLE 7

Growth Hormone Binding Protein Norms (Idiopathic GHD: GHBP Levels)

| Sex | Age | N | Mean −1 SD | Mean | Mean +1 SD |
|---|---|---|---|---|---|
| Male | 1 | 1 | — | 73.5 | — |
| Male | 3 | 3 | 40.3 | 63.7 | 100.7 |
| Male | 4 | 5 | 56.5 | 95.4 | 161.7 |
| Male | 5 | 3 | 79.5 | 96.5 | 117.1 |
| Male | 6 | 7 | 76.9 | 97.3 | 123.1 |
| Male | 7 | 1 | — | 59.4 | — |
| Male | 8 | 4 | 87.3 | 127.8 | 187.1 |
| Male | 9 | 5 | 81.9 | 128.9 | 203.0 |
| Male | 10 | 12 | 73.5 | 150.3 | 307.2 |
| Male | 11 | 9 | 108.5 | 177.5 | 290.2 |
| Male | 12 | 14 | 106.8 | 193.5 | 350.4 |
| Male | 13 | 16 | 102.1 | 164.4 | 264.6 |
| Male | 14 | 17 | 83.0 | 149.8 | 270.4 |
| Male | 15 | 17 | 122.4 | 191.1 | 298.3 |
| Male | 16 | 5 | 132.1 | 231.4 | 405.3 |
| Male | 17 | 4 | 136.0 | 165.0 | 200.2 |
| Male | 18 | 1 | — | 772.5 | — |
| Female | 3 | 1 | — | 55.8 | — |
| Female | 5 | 2 | 77.4 | 82.5 | 87.9 |
| Female | 6 | 3 | 117.8 | 157.6 | 210.8 |
| Female | 8 | 2 | 200.3 | 241.3 | 290.7 |
| Female | 9 | 2 | 43.8 | 59.7 | 81.3 |
| Female | 10 | 3 | 83.4 | 253.9 | 772.7 |
| Female | 1 | 10 | 91.0 | 162.5 | 290.3 |
| Female | 2 | 7 | 89.0 | 189.9 | 405.2 |
| Female | 13 | 2 | 86.6 | 154.5 | 275.9 |
| Female | 5 | 2 | 294.0 | 398.6 | 540.4 |

TABLE 8

Growth Hormone Binding Protein Norms (Turner Syndrome: GHBP Levels)

| Sex | Age | N | Mean −1 SD | Mean | Mean +1 SD |
|---|---|---|---|---|---|
| Female | 4 | 2 | 93.2 | 118.1 | 149.5 |
| Female | 5 | 4 | 84.1 | 108.3 | 139.4 |
| Female | 6 | 7 | 65.3 | 135.8 | 282.2 |
| Female | 7 | 4 | 97.5 | 146.1 | 218.9 |
| Female | 8 | 5 | 116.3 | 194.5 | 325.4 |
| Female | 9 | 10 | 107.9 | 199.0 | 367.2 |
| Female | 10 | 11 | 105.8 | 182.7 | 315.7 |

TABLE 8-continued

Growth Hormone Binding Protein Norms
(Turner Syndrome: GHBP Levels)

| Sex | Age | N | Mean −1 SD | Mean | Mean +1 SD |
|---|---|---|---|---|---|
| Female | 11 | 8 | 181.0 | 241.9 | 323.2 |
| Female | 12 | 8 | 139.4 | 286.4 | 588.2 |
| Female | 3 | 9 | 133.3 | 241.8 | 438.7 |
| Female | 14 | 15 | 222.2 | 321.4 | 464.8 |
| Female | 15 | 6 | 101.0 | 189.0 | 353.5 |
| Female | 16 | 6 | 147.4 | 237.6 | 383.0 |
| Female | 17 | 2 | 117.6 | 136.0 | 157.4 |

TABLE 9

Growth Hormone Binding Protein Norms
(Idiopathic Short Stature: GHBP Levels)

| Sex | Age | N | Mean −1 SD | Mean | Mean +1 SD |
|---|---|---|---|---|---|
| Male | 2 | 1 | — | 37.3 | — |
| Male | 3 | 8 | 46.0 | 100.2 | 218.5 |
| Male | 4 | 14 | 68.6 | 96.3 | 135.4 |
| Male | 5 | 24 | 61.0 | 86.1 | 121.6 |
| Male | 6 | 17 | 47.9 | 65.1 | 88.4 |
| Male | 7 | 35 | 52.9 | 83.0 | 130.0 |
| Male | 6 | 29 | 61.1 | 90.8 | 135.0 |
| Male | 9 | 25 | 64.7 | 100.7 | 189.3 |
| Male | 10 | 45 | 69.5 | 108.3 | 168.6 |
| Male | 11 | 43 | 67.0 | 106.1 | 168.0 |
| Male | 12 | 77 | 70.5 | 109.5 | 170.2 |
| Male | 13 | 73 | 73.5 | 117.9 | 189.3 |
| Male | 14 | 71 | 70.8 | 110.4 | 172.0 |
| Male | 15 | 51 | 64.7 | 113.8 | 200.3 |
| Male | 16 | 12 | 55.9 | 102.9 | 189.4 |
| Male | 17 | 5 | 80.3 | 112.7 | 158.2 |
| Male | 18 | 2 | 64.5 | 195.0 | 589.6 |
| Male | 19 | 1 | — | 93.8 | — |
| Male | 21 | 1 | — | 184.3 | — |
| Male | 23 | 1 | — | 36.9 | — |
| Female | 1 | 1 | — | 63.3 | — |
| Female | 2 | 2 | 56.8 | 57.4 | 58.0 |
| Female | 3 | 2 | 45.3 | 88.2 | 171.4 |
| Female | 4 | 2 | 87.1 | 88.0 | 89.0 |
| Female | 5 | 4 | 50.8 | 91.4 | 164.5 |
| Female | 6 | 5 | 45.6 | 84.7 | 157.4 |
| Female | 7 | 6 | 76.6 | 109.2 | 155.6 |
| Female | 8 | 9 | 75.4 | 116.0 | 178.6 |
| Female | 9 | 9 | 89.8 | 120.7 | 162.2 |
| Female | 10 | 19 | 102.1 | 174.9 | 299.7 |
| Female | 11 | 31 | 84.3 | 139.3 | 230.1 |
| Female | 12 | 20 | 89.4 | 150.1 | 252.2 |
| Female | 13 | 17 | 110.1 | 146.3 | 194.3 |
| Female | 14 | 9 | 102.1 | 160.9 | 253.7 |
| Female | 15 | 4 | 56.5 | 110.7 | 216.8 |
| Female | 16 | 2 | 148.1 | 182.2 | 224.1 |

FIG. 8 graphically illustrates the difference between normal GHBP and various etiologies. Plotted are GH binding protein levels from the National Cooperative Growth Study patients (log concentration of GHBP vs the age of patient). The crossbars represent mean values; solid vertical lines are plus or minus 1 SDs; dotted vertical lines are plus or minus two SDs. The separate black dots each represent one patient. (A) Idiopathic GHD for males; (B) Idiopathic GHD for females; (C) Idiopathic short stature for males; (D) Idiopathic short stature for females; (E) Turner Syndrome.

The clinical utility of the LIFA assay for distinguishing between normals and various etiologies can be seen in FIGS. 8(A–E). This is particularly pronounced in FIGS. 8C and D where the idiopathic short stature patients are predominantly below the mean for normal in both males and females. This provides a clinically valuable diagnostic test for evaluating the level of GHBP, and indirectly a presumptive determination of growth hormone receptor.

Ideopathic short stature is no longer ideopathic in that it can now be viewed as a state of relative GH resistance. Based upon the relative lack of GHBP this resistance is likely due to a deficiency in GH receptors that are capable of responding to GH. Current therapy of ISS involves daily hGH injections. One approach to the deficiency in GH receptors is to administer higher doses of GH to stimulate those receptors that are present. A dosage of from 1.1 to 10 times that now used is expected to increase the GH response. Alternatively, now that the underlying basis of ISS is revealed, new treatment options different from that currently used are suggested. In GH deficiency and Turner's syndrome, situations of normal GHBP and presumably normal GH receptor responsiveness, GHBP+GH is the logical treatment. In ISS patients, GHBP+GH may also be used to maximize the response by those GH receptors present. However, in ISS, IGF-1 therapeutic treatment is also indicated. IGF-1 is given alone or with IGF binding protein it may be coadministered with GH, and/or with GHBP. Since ISS patients have reduced GHBP, the GHBP+GH combination elevates the response by those GH receptors present. Administration of therapeutic amounts of IGF-1 or IGF-1 plus IGF BP elevates the effective serum IGF-1, thus partially circumventing the defective GH response and stimulating IGF-1 dependent responses.

What is claimed is:

1. A method of identifying candidates for growth hormone binding protein induced promotion of mammalian growth and anabolism comprising:
   a) measuring by a ligand-mediated immunofunctional assay the amount of growth hormone binding protein present in the biological fluids of a person suspected of being deficient in a growth hormone induced response, said ligand-mediated immunofunctional assay comprising:
      (1) contacting said biological fluids with: (i) a first antibody attached to a solid phase carrier, wherein said first antibody is specific for epitopes on said growth hormone binding protein such that in the presence of antibody the growth hormone binding sites remain available on the binding protein for binding to growth hormone, thereby forming a conjugate between said first antibody and said growth hormone binding protein; and (ii) growth hormone for a period of time sufficient to saturate all available growth hormone binding sites on said growth hormone binding protein thereby forming a saturated complex;
      (2) contacting said saturated complex with a detectably labeled second antibody which is specific for epitopes on said growth hormone which are available for binding when said growth hormone is bound to said growth hormone binding protein; and
      (3) quantitatively analyzing the amount of said second labeled antibody bound as a measure of said growth hormone binding protein in said biological fluids; and
   b) comparing the amount measured in a) to 90% of the average amount of growth hormone binding protein found in healthy individuals and if a) is less than said 90% of the average amount of growth hormone binding protein found in healthy individuals, considering said person as a candidate for the administration of growth hormone binding protein.

2. The method of claim 1 further comprising administering growth hormone binding protein to said candidate.

3. The method of claim 2 wherein growth hormone binding protein is complexed with growth hormone.

4. The method of claim 3 wherein said growth hormone binding protein and growth hormone are human growth hormone binding protein and human growth hormone.

5. The method of claim 4 wherein said growth hormone induced response is selected from the following: weight gain, bone growth, muscle growth and function, organ growth and function, skin growth, and the serum concentration of IGF-1.

6. The method of claim 4 wherein said candidates are human individuals diagnosed with growth hormone deficiency, Turner's syndrome or idiopathic short stature.

7. The method of claim 6 wherein the dose of growth hormone and growth hormone binding protein is from about 1 µg/kg/day to about 50 mg/kg/day of each protein.

8. The method of claim 6 wherein said candidates are human individuals diagnosed with idiopathic short stature, further comprising administering a therapeutically effective amount of insulin-like growth factor-1.

9. The method of claim 8 further comprising administering a therapeutically effective amount of insulin-like growth factor binding protein.

* * * * *